US012746357B2

(12) United States Patent
Runnels

(10) Patent No.: US 12,746,357 B2
(45) Date of Patent: Sep. 29, 2026

(54) SYSTEMS, DEVICES, AND TECHNIQUES FOR POSITIONING TUBES INCLUDING A SPLIT, ARTICULATING STYLET

(71) Applicant: Through the Cords, LLC, Salt Lake City, UT (US)

(72) Inventor: Sean Runnels, Salt Lake City, UT (US)

(73) Assignee: Through the Cords, LLC, Salt Lake City, UT (US)

( * ) Notice: Subject to any disclaimer, the term of this patent is extended or adjusted under 35 U.S.C. 154(b) by 852 days.

(21) Appl. No.: 17/827,065

(22) Filed: May 27, 2022

(65) Prior Publication Data

US 2022/0379058 A1 Dec. 1, 2022

Related U.S. Application Data

(60) Provisional application No. 63/193,994, filed on May 27, 2021.

(51) Int. Cl.
*A61M 16/04* (2006.01)
*A61B 1/267* (2006.01)

(52) U.S. Cl.
CPC ......... *A61M 16/0418* (2014.02); *A61B 1/267* (2013.01); *A61M 16/0488* (2013.01); *A61M 2205/584* (2013.01)

(58) Field of Classification Search
CPC .......... A61M 16/0418; A61M 16/0488; A61B 1/267
See application file for complete search history.

(56) References Cited

U.S. PATENT DOCUMENTS 2,541,402 A * 2/1951 Caine .................. A61B 1/2676 128/200.26
3,314,431 A * 4/1967 Smith, Jr. ......... A61M 16/0488 128/200.26
3,802,440 A * 4/1974 Salem ............... A61M 16/0429 138/120

(Continued)

FOREIGN PATENT DOCUMENTS

CN 112351726 A 2/2021

OTHER PUBLICATIONS

Extended European Search Report of the European Patent Office in related European Patent Appl. No. 22812259.4, dated Feb. 26, 2025, 9 pages.

(Continued)

*Primary Examiner* — Kathryn E Ditmer
(74) *Attorney, Agent, or Firm* — Bochner PLLC; Andrew D. Bochner

(57) ABSTRACT

Systems, devices, and techniques are described to position a tube in a trachea of a patient as part of an intubation procedure. An intubation system may include a stylet configured to position a tube in the trachea of the patient. The stylet may include an articulating segment and a support segment. The articulating segment may be configured to move between a first position and a second position in response to input received by the support segment. The movement of the articulating segment may be controllable by a caregiver. The intubation system may include a handle configured to receive an input from the caregiver and cause the stylet to move in response to the input.

13 Claims, 17 Drawing Sheets

(56) References Cited

U.S. PATENT DOCUMENTS

| | | | | |
|---|---|---|---|---|
| 4,672,960 | A * | 6/1987 | Frankel | A61M 16/0488 128/207.14 |
| 5,259,377 | A * | 11/1993 | Schroeder | A61M 16/0418 128/207.14 |
| 6,668,832 | B2 * | 12/2003 | Hipolito | A61M 16/04 128/207.14 |
| 7,959,642 | B2 * | 6/2011 | Nobis | A61B 17/3478 606/170 |
| 10,758,708 | B2 | 9/2020 | Gardner | |
| 2009/0065000 | A1 * | 3/2009 | Chen | A61M 16/0418 600/199 |
| 2009/0069632 | A1 * | 3/2009 | McIntyre | A61B 1/0055 600/146 |
| 2014/0123976 | A1 * | 5/2014 | Mccormick | A61M 16/0488 128/200.26 |
| 2014/0378766 | A1 * | 12/2014 | Lo | A61M 16/0488 600/120 |
| 2015/0099935 | A1 | 4/2015 | Runnels et al. | |
| 2016/0279365 | A1 * | 9/2016 | Esnouf | A61M 16/0418 |
| 2018/0110950 | A1 * | 4/2018 | Runnels | A61B 1/05 |
| 2018/0272092 | A1 | 9/2018 | Runnels | |
| 2019/0014980 | A1 | 1/2019 | Herskovic | |
| 2020/0023151 | A1 * | 1/2020 | Karlsson | A61B 1/0051 |
| 2020/0254204 | A1 | 8/2020 | Moffat et al. | |
| 2021/0093817 | A1 * | 4/2021 | Runnels | A61M 16/0488 |
| 2021/0213224 | A1 * | 7/2021 | Venticinque | A61M 16/0418 |
| 2024/0307644 | A1 * | 9/2024 | Horrisberger | A61M 16/0488 |

OTHER PUBLICATIONS

First Office Action of the Chinese Patent Office in related Chinese Appl. No. 202280047427.X, dated May 28, 2026, 20 pages.

* cited by examiner

SYSTEMS, DEVICES, AND TECHNIQUES FOR POSITIONING TUBES INCLUDING A SPLIT, ARTICULATING STYLET

CROSS-REFERENCE TO RELATED APPLICATIONS

This application claims the benefit of priority of U.S. provisional application No. 63/193,994 filed May 27, 2021, which is hereby incorporated herein by reference in its entirety.

FIELD OF THE INVENTION

The present disclosure is in the field of intubation devices. Specifically, systems, devices, and techniques for positioning endotracheal intubation tubes.

INTRODUCTION

Many surgical procedures are performed while the patient is under general anesthesia. During these procedures, the patient is given a combination of medications to cause a loss of consciousness and muscle paralysis. The medications that cause loss of consciousness and muscle paralysis may also interfere with the patient's ability to breathe. Patients often undergo tracheal intubation during these procedures to connect the patient with an external ventilator or breathing circuit. Patients may also be intubated for nonsurgical conditions in which enhanced oxygen delivery may be useful.

During tracheal intubation, an endotracheal tube may be placed in the patient's airway. Generally, the endotracheal tube is advanced through the patient's nose or mouth into the patient's trachea. The endotracheal tube may then be connected with an external ventilator or breathing circuit. The ventilator may then be enabled to breathe for the patient, delivering oxygen into the patient's lungs. Interruptions in oxygen delivery to the patient's lungs will reliably cause cardiac arrest, brain death, organ injury, and death in as little as 3-5 minutes. During intubation procedures, no oxygen is being delivered to the lungs while the breathing tube is inserted into the trachea. Placement of breathing tubes must be performed accurately and quickly in order to avoid major harm or death to patients. Difficulty placing a breathing tube is the most common preventable cause of brain death and death during general anesthesia.

Routine intubations can be performed by a single operator. Difficult intubations require advanced intubation equipment. Current advanced airway equipment is difficult to operate with just a single operator. Specifically, Tracheal Intubation is difficult, dangerous, and requires a great deal of training to achieve optimal outcomes. Tracheal intubation is the third most common medical procedure performed in the world and it is necessary for administration of mechanical ventilatory support (for example, for critically ill patients and major surgeries). Much of the equipment associated with such procedures is difficult to use. Accordingly, problems during intubation can lead to brain death, cardiac arrest, and death.

Intubation equipment that is intuitive and easy to use, easy to understand, and readily available is desirable to improve patient outcomes. In addition, intubation equipment that is ease to manufacture, iterate, and ship and store can reduce cost and improve immediate and equitable access to safe intubation worldwide.

Typically, intubation is a process which requires the achievement of two goals: (1) the vocal cords that mark the entrance to the trachea must be visualized; and (2) the trachea must be accessed by an endotracheal tube (ETT). Laryngoscopes are the most commonly used tool to visualize the tracheal entrance during intubation procedures.

Direct Laryngoscopy (DL) moves the tongue and lower jaw to allow the operator to directly view the vocal cords. Once the vocal cords are in view, tracheal access is along that same line of sight and is generally easy. However, the most common reason intubation fails with DL is due to a failure to gain a view around the corner of the upper airway not failure of tracheal access.

Consequently, Video Laryngoscopy (VL) was introduced to improve visualization as creating a direct line of sight to the vocal cords is known to be the most common reason for failure when using DL. Typically, a video laryngoscope has a camera on its tip allowing the operator to indirectly view the vocal cords around the corner of the upper airway, eliminating the need to gain a direct line of site view. VL assisted intubations has improved the ability to consistently view the vocal cords by allowing non line-of-site viewing around a corner. The ability for the operator to see around a corner has created a tracheal access problem as the operator now needs to work around a corner instead of in a straight line to gain access to the trachea. The most common reason for intubation to fail with VL is failure to access the trachea despite adequate visualization of the vocal cords. this is the paradox of VL, visualization has been made easy and improved by the VL's "look around the corner capability" but tracheal access is made harder as the operator now needs to maneuver around corners in order to gain access to the trachea. It is therefore advantageous to develop tracheal access equipment that is capable of steering around corners and moving though a serpentine pathway in order to move around the corners and curves of the airway to improve tracheal access. Furthermore it is advantageous to make access tools that can be fully operated with a single hand as advanced intubations can then be performed by a single operator. One hand operating the VL and one hand operating dynamically steerable tracheal access equipment.

There is clear correlation between the number of intubations attempts, major complications and mortality. In the event of an expected or unexpected difficult intubation it is important to have alternative advanced airway techniques readily available as a primary or rescue approaches to intubation. Common advanced intubation techniques include fiberoptic bronchoscopy and combined techniques using laryngoscopes with dynamic stylets. When managing difficult intubations, the optimal technique should be readily available, fast, effective, easy to use, and atraumatic.

The combined technique, utilizing both VL for visualization and dynamic stylets for tracheal access, aims to take advantage of the superior and panoramic visualization provided by VL and the active navigational abilities provided by dynamic stylets.

Recent literature suggests that combined techniques have scientifically proven advantages over VL with a rigid stylet or fiberoptic bronchoscopes alone when used to manage difficult intubations in terms of improved effectiveness and lower airway injury rates. Limiting factors preventing availability of combined technique for management of difficult intubation is the need for two operators to execute the technique and the expense of fiberoptic bronchoscopes.

It is therefore advantageous to design an articulating introducer that is easy and intuitive for use with a video laryngoscope, such that a video laryngoscope can be used for visualization of the tracheal entrance and the articulating introducer can provide active precise navigation to gain access to the trachea. It is also desirable to create equipment capable of dynamic navigation that can be operated with a single hand to enable single operator combined technique to be immediately available when difficult intubations are encountered.

Further, there is a desire for approaches that address these gaps that might make intubation less expensive, easier to perform, safer for patients, and produce more consistent high-quality outcomes.

SUMMARY

An aspect of the present disclosure may include an apparatus. The apparatus may include a stylet configured to mount an endotracheal tube, the stylet may include an articulating segment extending between a distal tip of the stylet and a joint of the stylet, the articulating segment may be configured to move relative to the joint; and a support segment extending between the joint of the stylet and a proximal tip of the stylet, the support segment may be configured to cause the articulating segment to move between a first position a second position. The apparatus may also include a handle, the handle may be configured to couple with the support segment of the stylet and cause at least a portion of the support segment to move that may result in the articulating segment of the stylet to move.

In an embodiment, the support segment includes a longitudinal split that divides the support segment into a first portion configured to be secured in a fixed position relative to the handle and a second portion configured to be moveable relative to the first portion and to the handle.

In another embodiment, movement of the second portion of the support segment may be configured to cause the articulating segment to move between the first position and the second position.

In yet another embodiment, the handle further includes an actuator configured to cause the second portion of the support segment to move relative to the first portion in response to movement of the actuator.

In a further embodiment, the actuator further includes a trigger configured to cause rotational movement in a disk in response to the trigger moving from a third position to a fourth position, where the disk may be configured to cause linear movement of the second portion of the support segment in response to the rotational movement of the disk, where the linear movement of the second portion of the support segment may be configured to cause the articulating segment to move between the first position and the second position.

In an embodiment, the disk may be configured to couple with a grooved track of the second portion of the support segment.

In another embodiment, the handle further includes a release mechanism configured to selectively couple with the handle with the stylet.

In yet another embodiment, the handle may be configured to couple with a plurality of longitudinal positions along the support segment of the stylet.

In a further embodiment, the handle may be configured to couple with a plurality of rotational positions of the support segment of the stylet.

In an embodiment, the stylet further includes at least one depth assessment band located at least partially on the articulating segment. In some examples of the apparatus, the stylet further includes a plurality of depth assessment bands located on the articulating segment, each depth assessment band visually distinct from an adjacent depth assessment band, a first depth assessment band located near the distal tip and having a first visual representation that may be configured to identify whether an insertion depth of the distal tip may be appropriate when positioned adjacent to an anatomical structure of a patient.

In another embodiment, the first depth assessment band indicates that the distal tip may have not been inserted to an appropriate depth.

In a further embodiment, the first depth assessment band indicates that the distal tip may have been inserted to an appropriate depth.

In an embodiment, each depth assessment band may have a visually distinct color or pattern from another depth assessment band.

In another embodiment, the anatomical structure of the patient may be a glottis of the patient.

In yet another embodiment, the anatomical structure of the patient may be a vocal cord of the patient.

In a further embodiment, the support segment includes a longitudinal split that divides the support segment into a first portion and a second portion, the first portion including a surface that forms a groove, and the second portion including a tongue configured to insert into the groove formed by the first portion.

In an embodiment, the first portion includes a first ledge, the second portion includes a second ledge, and the first ledge and the second ledge configured to secure the tongue of the second portion in the groove formed by the first portion.

In another embodiment, the first position of the articulating segment includes a first curve and the second position of the articulating segment includes a second curve.

In yet another embodiment, the first position of the articulating segment includes a first curve and the second position of the articulating segment includes a second curve and a third curve.

In an aspect of the present disclosure, the apparatus may include an articulating segment extending between a distal tip of the stylet and a joint of the stylet, the articulating segment configured to move relative to the joint and a support segment extending between the joint of the stylet and a proximal tip of the stylet, the support segment configured to cause the articulating segment to move between a first position a second position In an embodiment, the support segment includes a longitudinal split that divides the support segment into a first portion configured to be secured in a fixed position relative to the articulating segment and a second portion configured to be moveable relative to the first portion and to the articulating segment.

In another embodiment, movement of the second portion of the support segment may be configured to cause the articulating segment to move between the first position and the second position.

In yet another embodiment, the second portion of the support segment may be configured to move relative to the first portion of the support segment.

In a further embodiment, a plurality of depth assessment bands located on the articulating segment, each depth assessment band visually distinct from an adjacent depth assessment band, a first depth assessment band located near the distal tip and having a first visual representation that may be configured to identify whether an insertion depth of the distal tip may be appropriate when positioned adjacent to an anatomical structure of a patient.

In an embodiment, the first depth assessment band indicates that the distal tip may have not been inserted to an appropriate depth.

In another embodiment, the first depth assessment band indicates that the distal tip may have been inserted to an appropriate depth. In some examples of the apparatus, the first depth assessment band indicates that the distal tip may have been inserted too shallow in an airway of a patient. In some examples of the apparatus, the first depth assessment band indicates that the distal tip may have been inserted too deeply in an airway of a patient.

In yet another embodiment, each depth assessment band may have a visually distinct color or pattern from an other depth assessment band.

In a further embodiment, the anatomical structure of the patient may be a glottis of the patient.

In an embodiment, the anatomical structure of the patient may be a vocal cord of the patient.

In another embodiment, the support segment includes a longitudinal split that divides the support segment into a first portion and a second portion, the first portion including a surface that forms a groove, and the second portion including a tongue configured to insert into the groove formed by the first portion.

In yet another embodiment, the first portion includes a first ledge, the second portion includes a second ledge, and the first ledge and the second ledge configured to secure the tongue of the second portion in the groove formed by the first portion.

In a further embodiment, the first position of the articulating segment includes a first curve and the second position of the articulating segment includes a second curve.

In an embodiment, the first position of the articulating segment includes a first curve and the second position of the articulating segment includes a second curve and a third curve.

In an aspect of the present disclosure, the apparatus may include an articulating segment extending between a distal tip of the stylet and a first joint of the stylet, the articulating segment configured to move relative to the first joint, a support segment extending between the first joint of the stylet and a proximal tip of the stylet, the support segment including a second joint, and where the support segment is configured to cause the articulating segment to move and a sub-segment of the support segment to move, the articulating segment configured to move between a first position including a first curve a second position including a second curve, and the sub-segment configured to move between a third position including a third curve and a fourth position including a fourth curve In an embodiment, a structure to couple the first joint of the support segment with the second joint of the support segment, where the structure may be configured to cause the sub-segment to move between the third position including the third curve and the fourth position including the fourth curve.

In another embodiment, the support segment includes a longitudinal split that divides the support segment into a first portion configured to be secured in a fixed position relative to the articulating segment at the first joint and a second portion configured to be moveable relative to the first portion.

In yet another embodiment, the first portion of the support segment includes the second joint.

In a further embodiment, when the second portion of the support segment moves in a lateral direction, the articulating segment moves from the first position and towards the second position and the sub-segment of the support segment moves from the third position and toward the fourth position.

In an embodiment, the second curve of the articulating segment may have a first concavity and the fourth curve of the sub-segment of the support segment may have a second concavity.

In another embodiment, the second curve of the articulating segment and the fourth curve of the sub-segment of the support segment may be opposing curves that curve in different directions.

An aspect of the present disclosure may include an articulating endotracheal tube introducer. The articulating endotracheal tube introducer may comprise a shaft including a plurality of components. The plurality of components may include an articulating tip component extending between a distal tip of the shaft and a joint of the shaft, the articulating tip component configured to move relative to the joint; and a support component extending between the joint of the shaft and a proximal tip of the shaft. The articulating endotracheal tube introducer may further include a handle assembly removably attached to the shaft, the handle assembly configured to cause the articulating tip component to move between a first position a second position via a trigger.

In an embodiment, the articulating endotracheal tube introducer may further include a removable handle interface operably connected to one or more wires. The removable handle interface may move toward one of a distal point, or a proximal point of the shaft upon an input from a trigger via a trigger actuator.

In another embodiment, the handle assembly may be removably attached to the shaft via a release mechanism. The release mechanism may include one or more mounts configured to interface with one or more grooves located on the shaft.

In yet another embodiment, the one or more mounts may produce an audible click when engaging or disengaging with the one or more grooves.

In a further embodiment, the components may further include a tail portion component. The tail portion component may be configured to fold toward a distal end of the shaft Additional aspects related to this disclosure are set forth, in part, in the description which follows, and, in part, will be obvious from the description, or may be learned by practice of this disclosure.

It is to be understood that both the forgoing and the following descriptions are exemplary and explanatory only and are not intended to limit the claimed disclosure or application thereof in any manner whatsoever.

DETAILED DESCRIPTION

Figure 1:
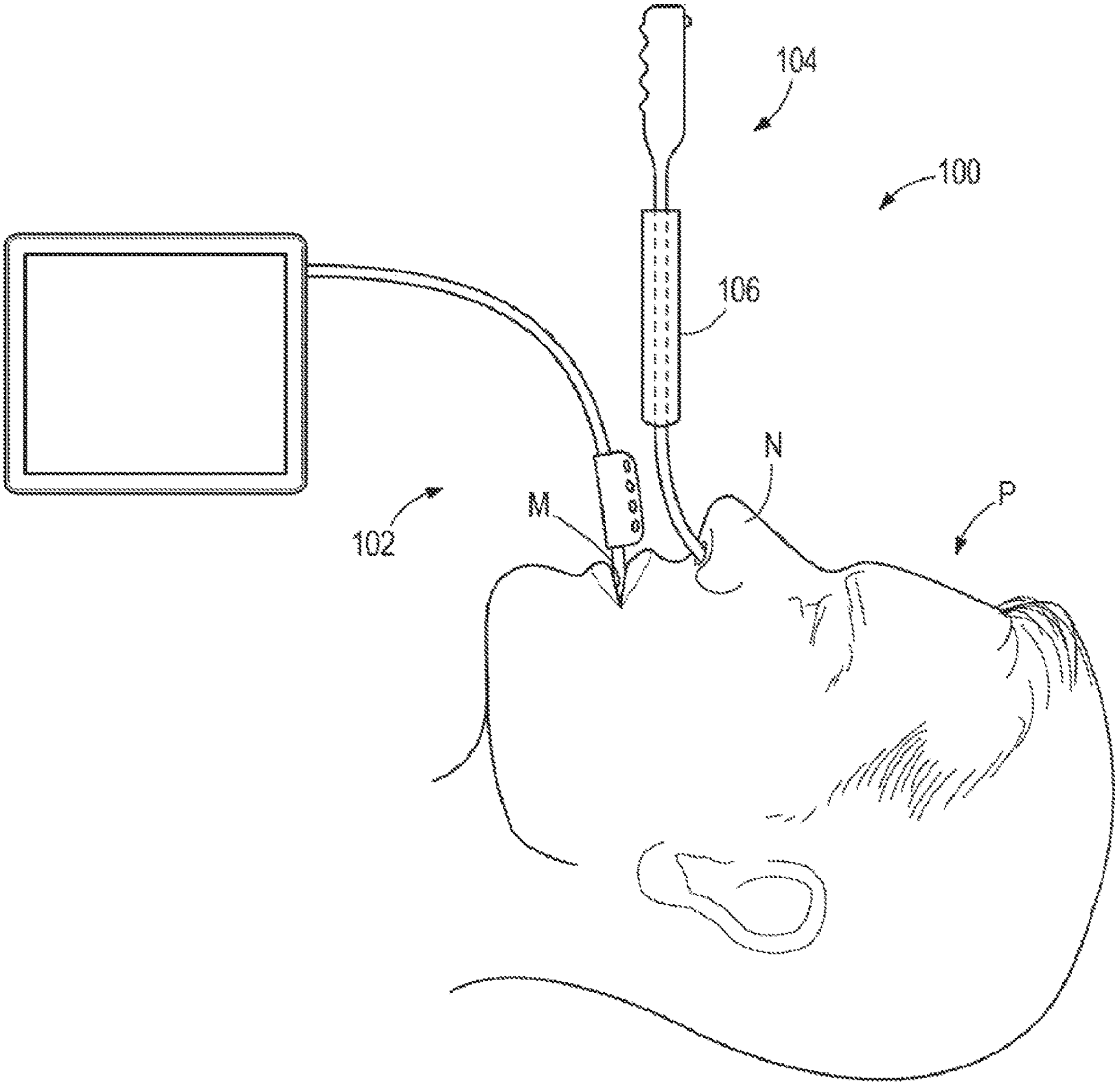
FIG. 1 illustrates an example of a tracheal intubation system used to intubate a patient that supports systems, devices, and techniques for positioning tubes in accordance with examples as disclosed herein.

In the following detailed description, reference will be made to the accompanying drawing(s), in which identical functional elements are designated with like numerals. The aforementioned accompanying drawings show by way of illustration, and not by way of limitation, specific aspects, and implementations consistent with principles of this disclosure. These implementations are described in sufficient detail to enable those skilled in the art to practice the disclosure and it is to be understood that other implementations may be utilized and that structural changes and/or substitutions of various elements may be made without departing from the scope and spirit of this disclosure. The following detailed description is, therefore, not to be construed in a limited sense.

During some medical procedures or medical conditions, a patient may have challenges breathing. In such circumstances, a caregiver may insert a tube into the throat and the windpipe of the patient to make it easier to get air into and out of the lungs of the patient. The tube may be coupled with a ventilator that is configured to pump air into and out of the lungs of the patient. During an intubation process, the endotracheal tube should be carefully advanced through the patient's pharynx and placed through the vocal cords into the trachea. The intubation process may interfere with the patient's ability to breathe independently and thus deliver oxygen to the body independently. If the patient is without oxygen for more than two or three minutes, tissue injury may occur, which can lead to death or permanent brain damage. Accordingly, the intubation process should be performed quickly and accurately.

The process of navigating a tube into the windpipe into the windpipe of the patient may be referred to as intubation. During an intubation procedure, a stylet or guide may be used by a caregiver to navigate and position the tube in a desirable location. The process of inserting the stylet into the patient or the positioning of the tube in the airway of the patient may cause damage or trauma to the patient. For example, the pathway from the mouth or nose into the trachea is often not entirely straight and there may be curves in the anatomy of the patient. When navigating those curves, the stylet may impact parts of the patient's airway tissue. This can make intubation difficult or even impossible, and thereby put the patient at risk for harm or death. This may also damage the patient's tissue causing harm. In other examples, if the tube is positioned too deeply into the windpipe of the patient it may cause unnecessary trauma or damage. In yet further examples, if the tube is positioned too shallowly in the windpipe of the patient it may come out of the trachea, placing the patient at risk of harm or death.

Systems, devices, and techniques are described to position a tube in the trachea of the patient that reduce damage or trauma to the patient, as compared with other systems, devices, and techniques. An intubation system may include a stylet configured to assist in navigation and placement of a tube in the trachea of the patient. The stylet may include an articulating segment and a support segment. The articulating segment may be configured to move between a first position and a second position in response to input received by the support segment. The articulation or movement of the articulating segment may be controllable by a caregiver to reduce contact between the stylet and the anatomy of the patient during the intubation process and to thereby reduce trauma or damage as well as assist in navigation into the trachea. The intubation system may include a handle configured to receive an input from the caregiver and cause the stylet to move between the first position and the second position.

FIG. 1 illustrates an example of a tracheal intubation system 100 used to intubate a patient P that supports systems, devices, and techniques for positioning tubes in accordance with examples as disclosed herein. The intubation system 100 may include a laryngoscope 102, an articulating stylet 104, and an endotracheal tube 106. The patient P may include the mouth M and the nose N. The laryngoscope 102 may be inserted into the mouth M of the patient P, the articulating stylet 104 may be inserted into the nose N of the patient P, and the endotracheal tube 106 may be mounted on the articulating stylet 104. In other examples, the articulating stylet 104 may be inserted into the mouth M of the patient P.

The patient P may be an example of a person or animal who is being intubated. Although the intubation system 100 is particularly useful to intubate a patient with a difficult airway, the intubation system 100 may also be used on a patient with a normal airway. Examples of patient P may include adults, children, infants, elderly people, obese people, people with tumors affecting the head or neck, and people with unstable cervical spines. In some examples, the intubation system 100 may be used to intubate animals with normal or difficult airways.

The laryngoscope 102 may be a medical instrument configured to permit a caregiver to directly or indirectly view, among other things, the glottis of the patient P. The laryngoscope 102 may include a blade, an optical capture device, and light source. In some examples, the blade is configured to be inserted through the mouth M of the patient P and positioned so that the glottis is in the field of view of the optical capture device. The image captured by the laryngoscope 102 is viewed from a position that is external to the patient P and may be viewed on an external display device, such as a screen.

The articulating stylet 104 may include a thin, flexible tube that may be directed and advanced into the airway of the patient P. The articulating stylet 104 may be configured to serve as a guide in the placement of the endotracheal tube 106. The articulating stylet 104 may be configured to be coupled with a handle that includes a control mechanism that is configured to cause a tip of the articulating stylet 104 to move between a first position and a second position. The articulating stylet 104 is configured to be viewed with the laryngoscope 102 during the intubation procedure.

The endotracheal tube 106 may be a hollow tube that is configured to be placed in the airway of the patient P. When the patient P is intubated, one end of the endotracheal tube 106 is disposed inside the trachea of the patient P and the other end is connected to an external ventilator or breathing circuit. The endotracheal tube 106 is configured to occlude the airway of the patient P. Thus, gases (e.g., room air, oxygenated gases, anesthetic gases, expired breath, etc.) may flow into and out of the trachea of the patient P through the endotracheal tube 106. In some examples, the endotracheal tube 106 may be connected to a breathing circuit, including for example a machine-powered ventilator or a hand-operated ventilator. In other examples, the patient P may breathe through the endotracheal tube 106 spontaneously.

The endotracheal tube 106 may be configured to be mounted on the articulating stylet 104 by sliding over the tip and along the shaft of the articulating stylet 104. After a caregiver has positioned the tip of the articulating stylet 104 in the trachea of the patient P, the endotracheal tube 106 is advanced over the shaft of the articulating stylet 104 and into the trachea of the patient P. In this manner, the articulating stylet 104 guides the endotracheal tube 106 into the proper location in the trachea of the patient P.

Figure 2:
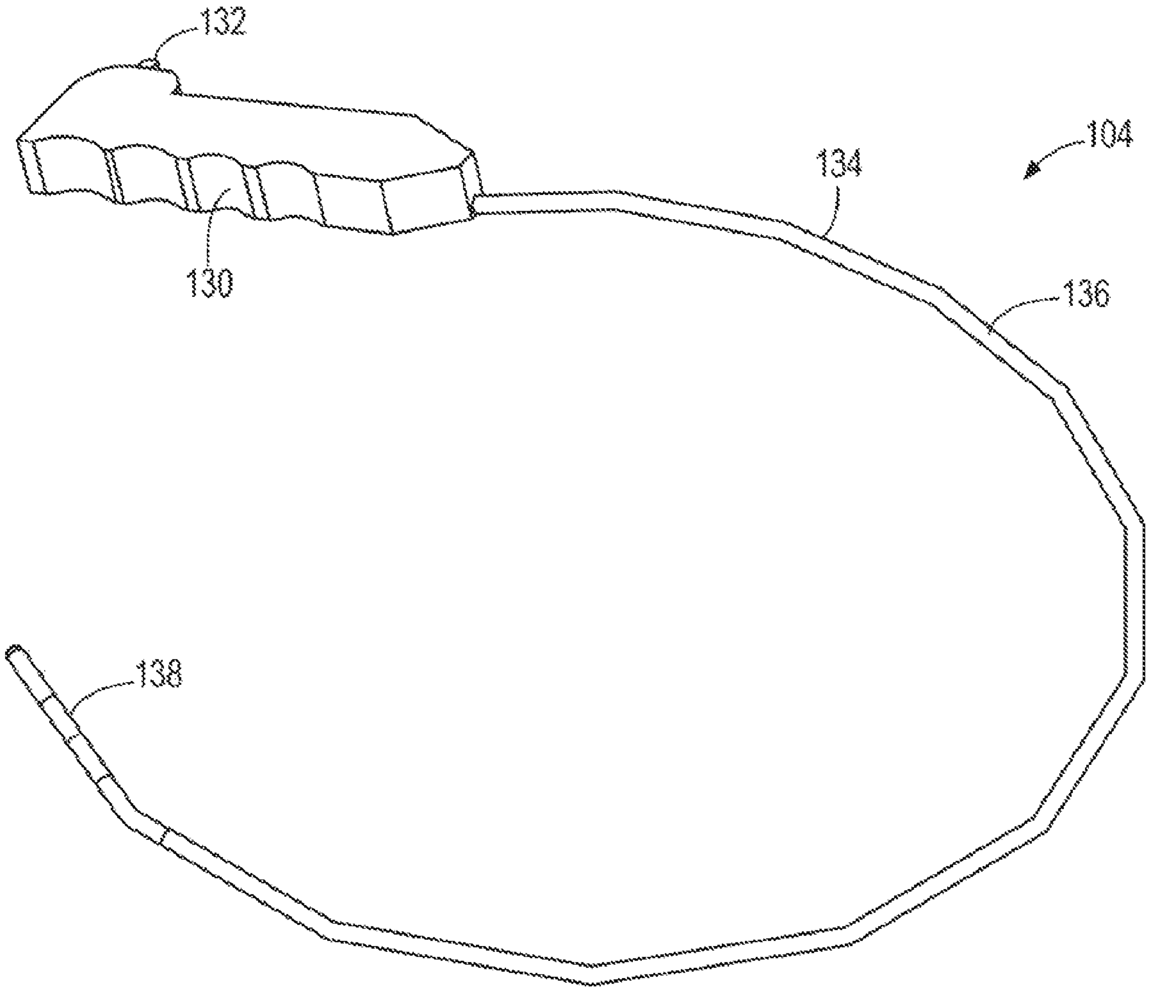
FIG. 2 illustrates a perspective view of an example of an articulating stylet that supports systems, devices, and techniques for positioning tubes in accordance with examples as disclosed herein.

FIG. 2 illustrates a perspective view of an example articulating stylet 104 that supports systems, devices, and techniques for positioning tubes in accordance with examples as disclosed herein. The articulating stylet 104 may be configured to guide an endotracheal tube into the trachea of a patient. The articulating stylet 104 may include a handle 130 and a shaft 134. The handle 130 may include a tip control mechanism 132.

In some examples, the handle is configured to be held in a hand of a caregiver. In some examples, the cross section of the handle 130 is cylindrical. In some examples, the cross section of the handle 130 is rectangular. In other examples, the cross section of the handle 130 is rectangular with rounded corners. In some examples, the handle 130 includes one or more molded finger grips.

The tip control mechanism 132 is configured to control the movement of the tip 138 of the shaft 134. In some examples, the tip control mechanism 132 is configured to be manipulated by a thumb of a caregiver. In other examples, the tip control mechanism 132 is configured to be manipulated by one or more fingers or the palm of a caregiver. In some examples, the tip control mechanism 132 may include a trigger and one or more other components to cause movement by the articulating stylet 104.

In some examples, the tip control mechanism 132 is a switch that has three physical positions. Each physical position corresponds to a movement instruction for the tip 138. For example, one physical position instructs the tip 138 to move or pivot in a first direction, a second physical position instructs the tip 138 to move or pivot in a second direction, and a third physical position instructs the tip 138 to remain stationary. In other examples, the tip control mechanism 132 may have fewer or more than three physical positions.

In some examples, the tip control mechanism 132 is a potentiometer and behaves in a manner similar to a joystick. In such examples, the tip 138 may be articulated in a first direction by actuating the potentiometer in one direction and the tip 138 is articulated in a second direction by actuating the potentiometer in another direction. Depending on the magnitude of actuation of the potentiometer, the tip 138 may pivot to a greater or lesser degree. When the potentiometer is not actuated, the tip 138 is not articulated. In other examples, the tip control mechanism 132 is implemented with one or more buttons or touch sensors. When one of the buttons or touch sensors is activated, the tip 138 is articulated in a specific direction. In some examples, the tip control mechanism 132 is a wheel, trigger, or lever. Still other examples of tip control mechanism 132 are possible.

The shaft 134 may include an exterior surface 136 and a tip 138. The shaft 134 is configured to be inserted into the nose or mouth of a patient and directed through the glottis of the patient and into the trachea of the patient.

At portion positioned away from the tip 138, the shaft 134 may be coupled with the handle 130. In some examples, the shaft 134 is between two to three feet in length and has a diameter of 3⁄16 of an inch. However, in other embodiments, the shaft 134 may have any suitable diameter. In other examples, especially those directed towards pediatric patients, the shaft 134 may have a smaller diameter. Other examples, with smaller or greater lengths or smaller or greater diameters are possible as well.

In some examples, the shaft 134 has a tubular shape and is formed from a flexible material that is configured to adapt to the shape of the airway of the patient. In some examples, the cross-section of the shaft 134 has an oblong shape. Other examples of shaft 134 with other shapes are possible.

In some examples, the exterior surface 136 comprises a single, continuous, uniform material. In some examples, the exterior surface 136 has non-stick properties. For example, in some examples the exterior surface 136 is formed from polytetrafluoroethylene. In other examples, the exterior surface 136 is configured to receive a lubricant. Other examples of the exterior surface 136 are possible as well. Because the exterior surface 136 is formed from a continuous material, the exterior surface 136 does not have any seams. Accordingly, the exterior surface 136 can be quickly and inexpensively cleaned. For example, the exterior surface 136 may be sterilized without the use of expensive and time-consuming sterilization equipment (e.g., an autoclave).

In some examples, the tip 138 is configured to move or pivot independently from the remainder of shaft 134. In some examples, the tip 138 is configured to reduce trauma as it moves through the nose or mouth into the upper airway and advances into the trachea of the patient. In some examples, the tip 138 is contained within the exterior surface 136. In some examples, the tip 138 has a blunt rounded shape. In some examples, the tip 138 does not have edges, corners, or crevices that may potentially injure the patient. Still other examples of the tip 138 are possible.

In some examples the shaft 134 and tip 138 do not contain, and are free of, a camera, light source, or other mechanism to illuminate or capture images of the patient. Accordingly, in some examples the design of the exterior surface 136 of the shaft 134 and tip 138 is designed to reduce trauma and simplify sterilization. The design of the exterior surface 136 of the shaft 134 and tip 138 is not constrained by the requirements of a camera, light source, or optical fibers, such as lenses, heating elements for defogging, and lumens for directing water or suctioning to clear the field of view.

Figure 3:
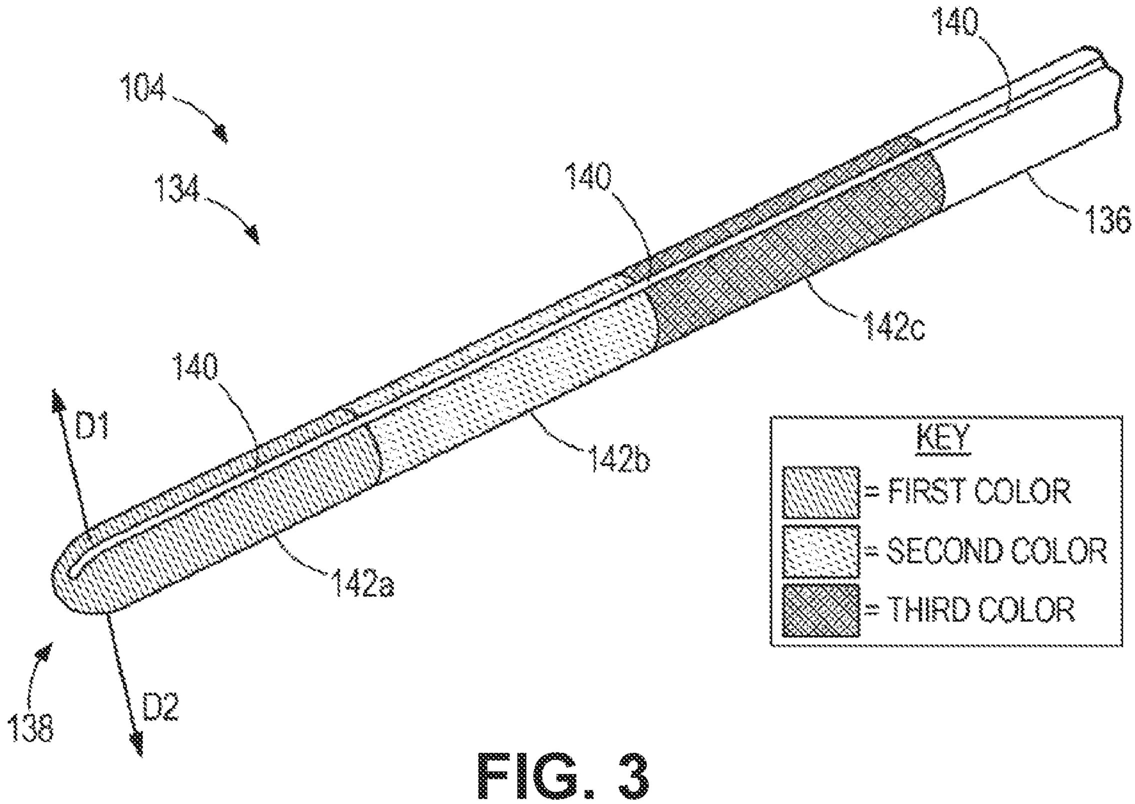
FIG. 3 illustrates a perspective view of depth assessment bands of the articulating stylet of FIG. 2 that supports systems, devices, and techniques for positioning tubes in accordance with examples as disclosed herein.

FIG. 3 illustrates a perspective view of depth assessment bands 142 of the articulating stylet 104 of FIG. 2 that supports systems, devices, and techniques for positioning tubes in accordance with examples as disclosed herein. The articulating stylet 104 may include an orientation mark 140 and one or more depth assessment bands 142*a*, 142*b*, or 142*c* (collectively depth assessment bands 142).

The orientation mark 140 may be an indicator that is on or visible through the exterior surface 136 and is configured to be visible when the articulating stylet 104 is viewed with the laryngoscope 102. The orientation mark 140 is configured to convey information about the radial orientation of the articulating stylet 104. In some examples, the orientation mark 140 may convey information about which direction the articulating segment of the articulating stylet may move between the first position and the second position. In some examples, the orientation mark 140 is a straight line the starts at or near the end of tip 138 and continues longitudinally along the length of shaft 134. In some examples, the orientation mark 140 is present throughout the entire length of the shaft 134. In other examples, the orientation mark 140 is present along a portion of the shaft 134. In some examples, the orientation mark 140 is radially aligned with the direction D 1, in which the tip 138 is configured to move. In this manner, a caregiver is able to view the orientation mark 140 on the display device of the laryngoscope 102 to determine the direction the tip 138 will move if it is pivoted. Thus, a caregiver is able to quickly direct the articulating stylet 104 into the trachea of the patient without erroneously pivoting the tip 138, which may result in delay or trauma to the patient.

In some examples, the orientation mark 140 is a dashed line or a series of dots. In some examples, the orientation mark 140 is not radially aligned with the direction D 1 but still conveys the orientation information necessary for a caregiver to direct the articulating stylet 104. In some examples, multiple orientation marks are included.

In some examples, the articulating stylet 104 includes one or more depth assessment bands 142. In the example, the articulating stylet 104 includes a first depth assessment band 142*a*, second depth assessment band 142*b*, and a third depth assessment band 142*c*. The depth assessment bands 142 are visual indicators that are on or visible through the exterior surface 136 and are configured to be visible when the articulating stylet 104 is viewed with the laryngoscope 102. The depth assessment bands 142 are configured to convey information about the placement of the articulating stylet 104 relative to the anatomical landmarks of the patient, such as the vocal cords, that are also visible through the laryngoscope 102. The depth assessment bands 142 are also configured to convey information about the longitudinal distance to the end of the tip 138.

The depth assessment bands 142 may provide a qualitative assessment of an insertion depth of the stylet 104 (e.g., and any tube positioned on the stylet) in the patient, such as when the one or more depth assessment bands 142 are compared to an anatomical structure of the patient. The qualitative assessment properties of the one or more depth assessment bands 142 may be different than quantitative assessments provided by other types of markings. In some instances, this may allow rapid, yet accurate evaluation of the placement of a stylet or a tube during a medical procedure. In some such procedures, accurate tube placement is required, but time may not be available for measurements or reference to quantitative indicators of placement. The depth assessment bands 142 may provide for qualitative evaluation of placement which may require less time than quantitative indicia. In some examples, the stylet or the tube may alternatively or additionally include one or more quantitative depth assessment bands, such as numeric depth assessment bands configured to provide a quantitative assessment of an insertion depth of the stylet or the tube in the patient.

The numeric depth assessment bands may quantify a numeric depth (e.g., 5 mm) associated with the insertion of the stylet or the tube when compared to a reference point (e.g., an anatomical reference point on a body of the patient or another reference). An example of such numeric depth assessment bands may be markings such as tic marks with numbers or other markings that indicate a measured distance from a set reference point (e.g., the end of the stylet or the tube). One challenge with quantitative markings may be that it may take the user at least two steps to determine what action is needed. First, the user may identify the number indicated by the quantitative marking. Second, the user may compare that number to ranges of values to determine what action may be taken with the placement of the stylet or the tube. The comparison may include comparing the numeric value to an actual table or it may be done in the head of the user. In contrast, the qualitative depth assessment bands 142 of the stylet or the tube may indicate attributes or properties of the insertion depth of the stylet or the tube in the patient to the user in as little as a single glance. For example, qualitative depth assessment bands may indicate whether the insertion depth of the stylet or the tube is within a zone of safety, a zone of warning, a zone of danger, other zones or types of zones, or a combination thereof. Qualitative assessment bands directly indicate the range of values and indicate what actions can be taken. Thus, qualitative assessment bands may allow a user to make an assessment in a single step of identifying the qualitative assessment band.

Adjacent depth assessment bands 142 may be visually distinct from each other so that a caregiver who views a part of one of the depth assessment bands 142 from the laryngoscope is able to identify specifically which of the depth assessment bands 142 is in the field of view. In some examples, the depth assessment bands 142 may be continuous regions, and it may not be necessary for a caregiver to advance or retract the articulating stylet 104 to bring one of the depth assessment bands 142 into the field of view of the laryngoscope 102, which would create a risk of trauma to the patient or inadvertent removal of the articulating stylet 104 from the trachea of the patient. Nor does a caregiver have to remember or count the depth assessment bands 142 as they pass through the field of view. In this manner, the depth assessment bands 142 may reduce trauma to the patient and allow a caregiver to focus on using the articulating stylet 104 rather than counting depth assessment bands 142. Further, using the depth assessment bands 142 in this manner may reduce the time necessary to complete a tracheal intubation procedure.

In some examples, the depth assessment bands 142 are continuous regions of color that extend along a portion of the length of the shaft 134. For example, the first depth assessment band 142*a* is a first color, the second depth assessment band 142*b* is a second color, and the third depth assessment band 142*c* is a third color. In other examples, the depth assessment bands 142 are continuous regions of visually distinct patterns rather than colors. In some examples, the depth assessment bands 142 include both visually distinct patterns and colors. Yet other examples are possible as well.

In some examples, the lengths of the depth assessment bands 142 are selected based on the clinical precision required for the intubation procedure in which the articulating stylet 104 is intended and the distance into the trachea of the patient a caregiver wishes to insert the tip 138. For example, a caregiver may wish to insert the tip 138 two to four centimeters into the trachea of an adult patient. In some examples for adult patients, the length of each of the depth assessment bands 142 is two centimeters. In this manner, the caregiver will know that the tip 138 is properly inserted into the trachea of the patient when any part of the second depth assessment band 142*b* is aligned with the entrance of the trachea of an adult patient (i.e., the patient's vocal cords).

Similarly, in some examples for pediatric patients, the lengths of the depth assessment bands 142 are adapted to the shorter tracheas of those pediatric patients. For example, a caregiver may wish to insert the tip 138 one to two centimeters into the trachea of the pediatric patient. In some examples for pediatric patients, the length of each depth assessment band 142 is one centimeter. In this manner, the caregiver will know that the tip 138 is properly inserted into the trachea of the patient when any part of the second depth assessment band 142*b* is aligned with the entrance of the trachea of the pediatric patient (i.e., the patient's vocal cords).

In some examples, the colors of the depth assessment bands 142 convey information about whether the tip 138 is properly positioned. In some example examples, the first depth assessment band 142*a* is yellow, the second depth assessment band 142*b* is green, and the third depth assessment band 142*c* is red. The yellow color of the first depth assessment band 142*a* may convey to a caregiver to use caution in advancing the tip 138 because it is not yet properly positioned. The green color of the second depth assessment band 142*b* may convey success to a caregiver because the tip 138 appears to be properly positioned (e.g., a zone of safety). The red color of the third depth assessment band 142*c* may convey warning to a caregiver because the tip 138 may be positioned too deeply in the trachea of the patient, potentially causing trauma.

Figure 5:
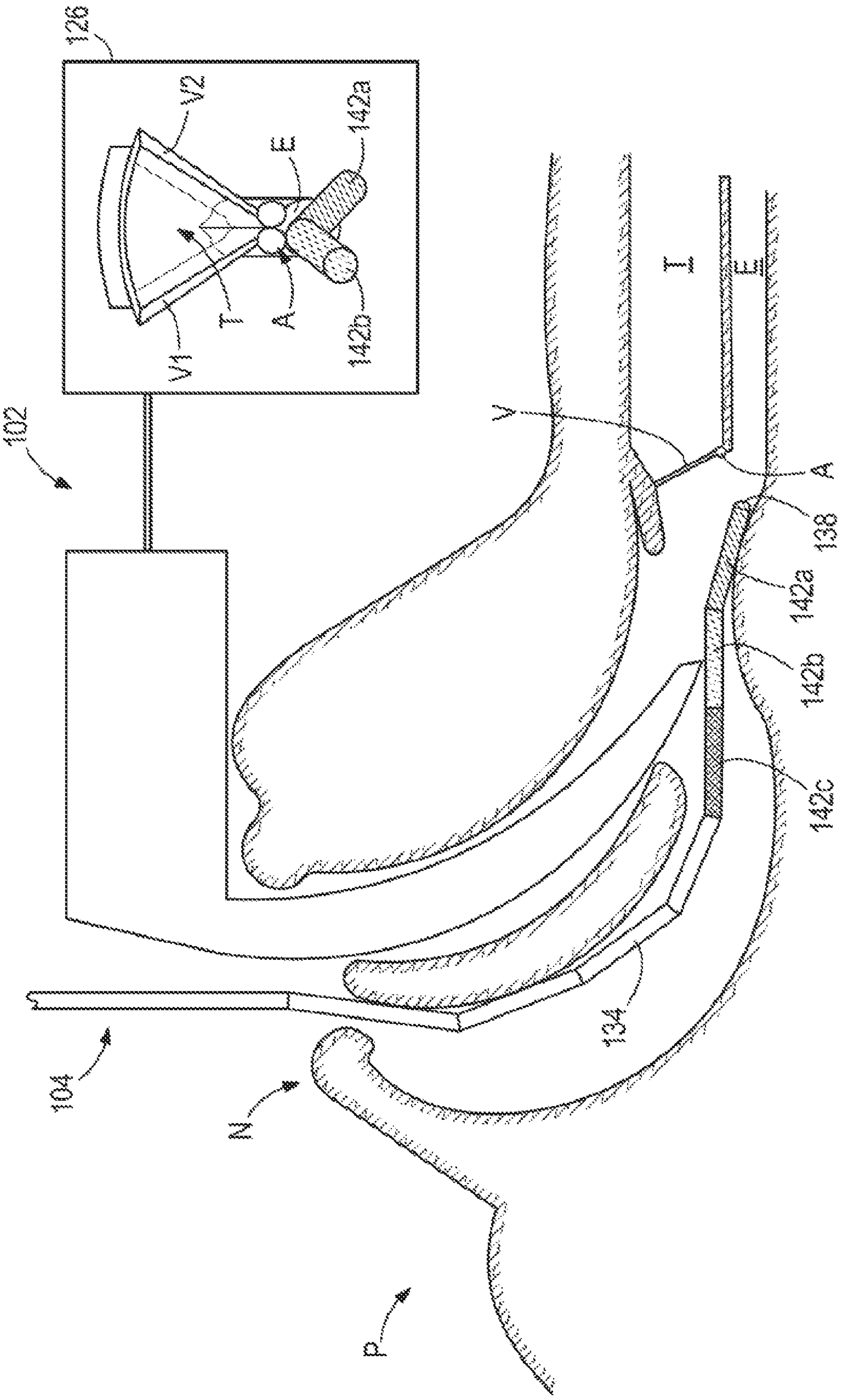
FIGS. 5-11 illustrate cross-sectional views of a patient during an intubation procedure using an example of a tracheal intubation system that support systems, devices, and techniques for positioning tubes in accordance with examples as disclosed herein.

Although the example shown in FIG. 5 includes three depth assessment bands 142, other examples that include fewer or more depth assessment bands 142 are possible as well. In some examples, the depth assessment bands 142 are uniform in length. In other examples, one or more of the depth assessment bands 142 has a different length than the other depth assessment bands 142. For example, in applications requiring precision, one of the depth assessment bands 142 is shorter in length than the other depth assessment bands 142. Accordingly, when that one of the depth assessment bands 142 is aligned with the entrance to the trachea of a patient (i.e., the vocal cords), a caregiver is able to determine the depth of the tip 138 with greater precision.

Although the example of the depth assessment bands 142 shown in FIG. 3 relates to an articulating stylet 104, the depth assessment bands 142 can also be used with other stylets. For example, in some examples, the depth assessment bands 142 are used with a stylet that does not articulate. In these examples, the stylet is similar to the articulating stylet 104 described herein, except that the tip does not articulate and the components that control the tip are not included. In these examples, the stylet still includes the depth assessment bands 142, which can be viewed with the laryngoscope 102 to determine the position of the non-articulating tip of the stylet relative to various anatomical landmarks.

Although the examples described herein relate to placement of an endotracheal tube, the depth assessment bands are not limited to use in airway devices. In some examples, the depth assessment bands 142 are included on other medical devices to guide the proper placement of those medical devices as well. For example, in some examples, the depth assessment bands 142 are included in central venous catheters, endoscopic devices, devices placed in the gastrointestinal tract, devices placed inside the cardiovascular system, devices placed inside the urinary system, devices placed inside of the ears, devices placed inside of the eyes, devices placed in the central nervous system, devices placed inside of the abdomen, devices placed inside the chest, or devices placed inside the musculoskeletal system. In these examples, the depth assessment bands 142 are configured to be compared to various. In these examples, the depth assessment bands 142 are configured to convey information about the placement of the device relative to various anatomical landmarks compared to other organ systems inside the body or even outside of the body. In some of these examples, the depth assessment bands 142 may be compared with different references (e.g., different anatomical structures such as the skin of the patient, the mouth of the patient, or other internal structures of the patient. Additionally, in some examples, the depth assessment bands 142 are included on non-medical devices in which depth control is desired. For example, the depth assessment bands 142 can be included in industrial devices, such as devices for the inspection of machinery or physical structures, and devices for the proper placement of fasteners or other industrial or physical parts.

Figure 4:
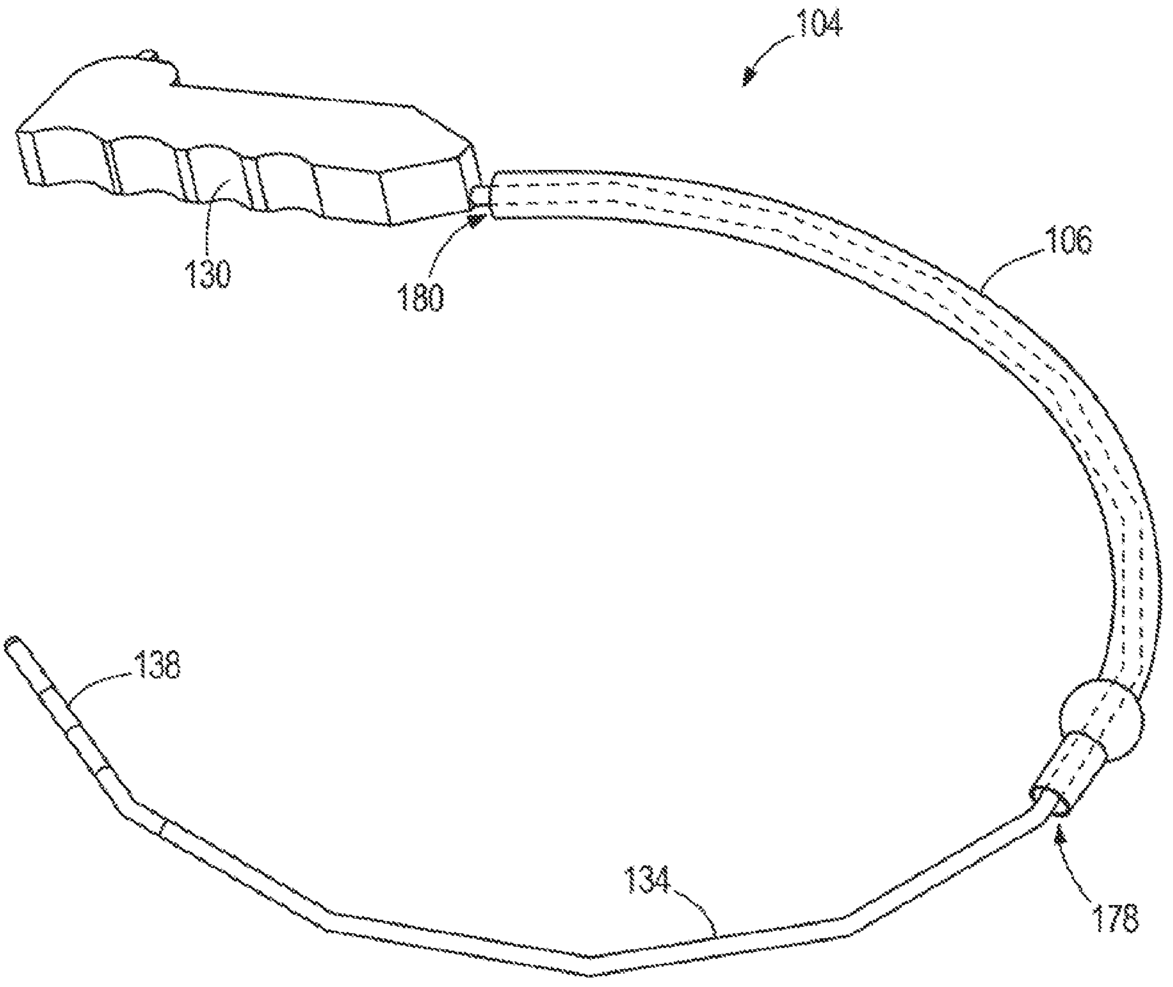
FIG. 4 illustrates an example of an endotracheal tube mounted on an articulating stylet that supports systems, devices, and techniques for positioning tubes in accordance with examples as disclosed herein.

FIG. 4 illustrates an example of an endotracheal tube 106 mounted on an articulating stylet 104 that supports systems, devices, and techniques for positioning tubes in accordance with examples as disclosed herein. The endotracheal tube 106 may include a pipe with a first end 178 and a second end 180. The shaft 134 of the articulating stylet 104 may pass through the endotracheal tube 106. The endotracheal tube 106 may be oriented so that the first end 178 is nearer to the tip 138 of the articulating stylet 104 and the second end 180 is nearer to the handle 130 of the articulating stylet 104.

FIGS. 5-11 illustrates cross-sectional views of a patient during an intubation procedure using an example tracheal intubation system that support systems, devices, and techniques for positioning tubes in accordance with examples as disclosed herein. Each of the figures illustrate different parts of the intubation procedure and how an articulating stylet can be used to position the tube.

FIG. 5 illustrates a cross-sectional view of a patient P during an intubation procedure using an example tracheal intubation system that supports systems, devices, and techniques for positioning tubes in accordance with examples as disclosed herein. The shaft 134 of the articulating stylet 104 is being advanced into the patient P through the nose N of the patient P. The tip 138 is in the field of view of the optical capture device of the laryngoscope 102. The first depth assessment band 142*a* and the second depth assessment band 142*b* are visible on screen 126. Screen 126 displays that the tip 138 is currently directed towards the esophagus E.

Figure 6:
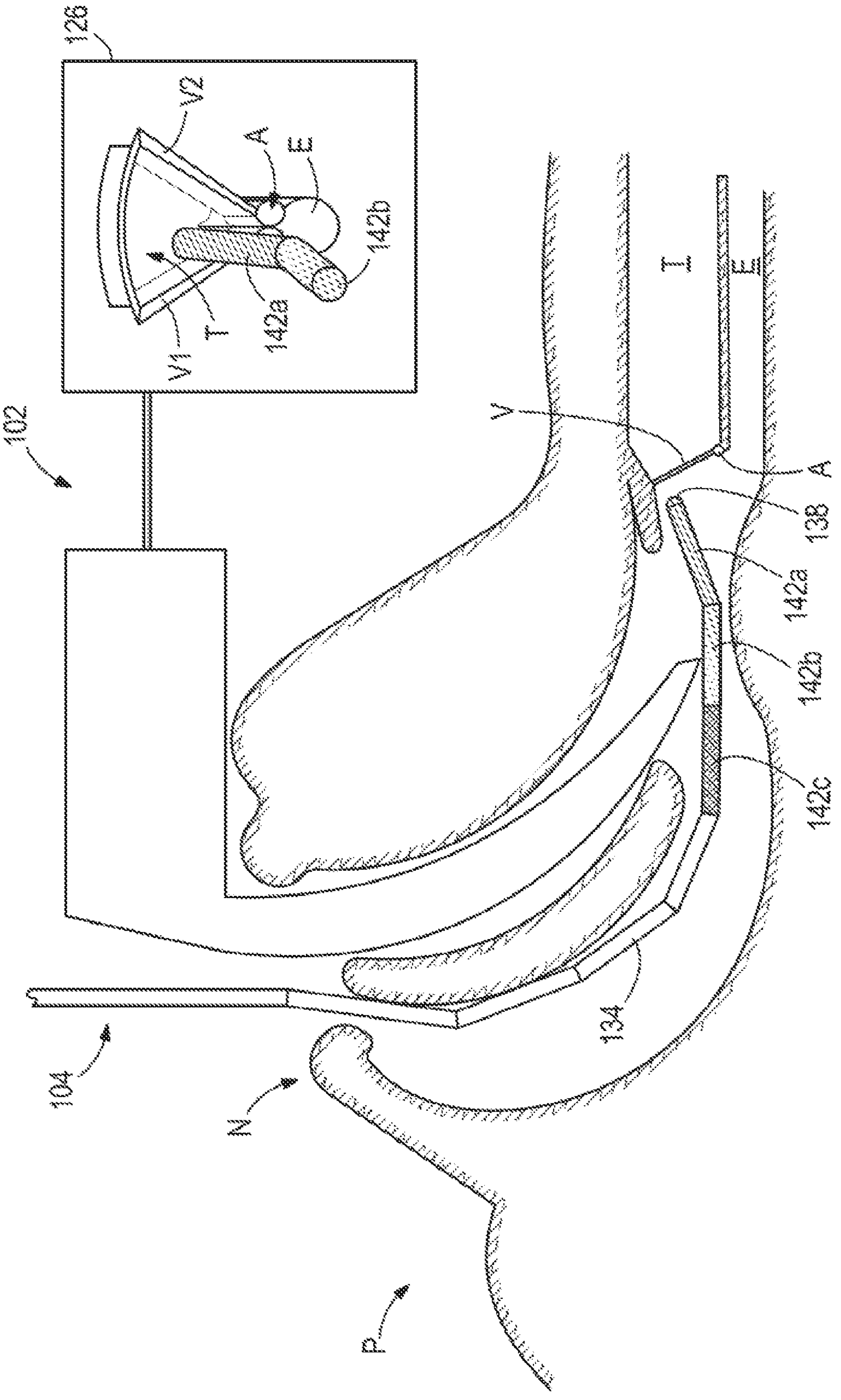

FIG. 6 illustrates a cross-sectional view of a patient P during an intubation procedure using an example tracheal intubation system that supports systems, devices, and techniques for positioning tubes in accordance with examples as disclosed herein. The tip 138 of the articulating stylet 104 is pivoted up as compared to its position in FIG. 5. The screen 126 shows that the tip 138 is now directed towards the entrance of the trachea T.

Figure 7:
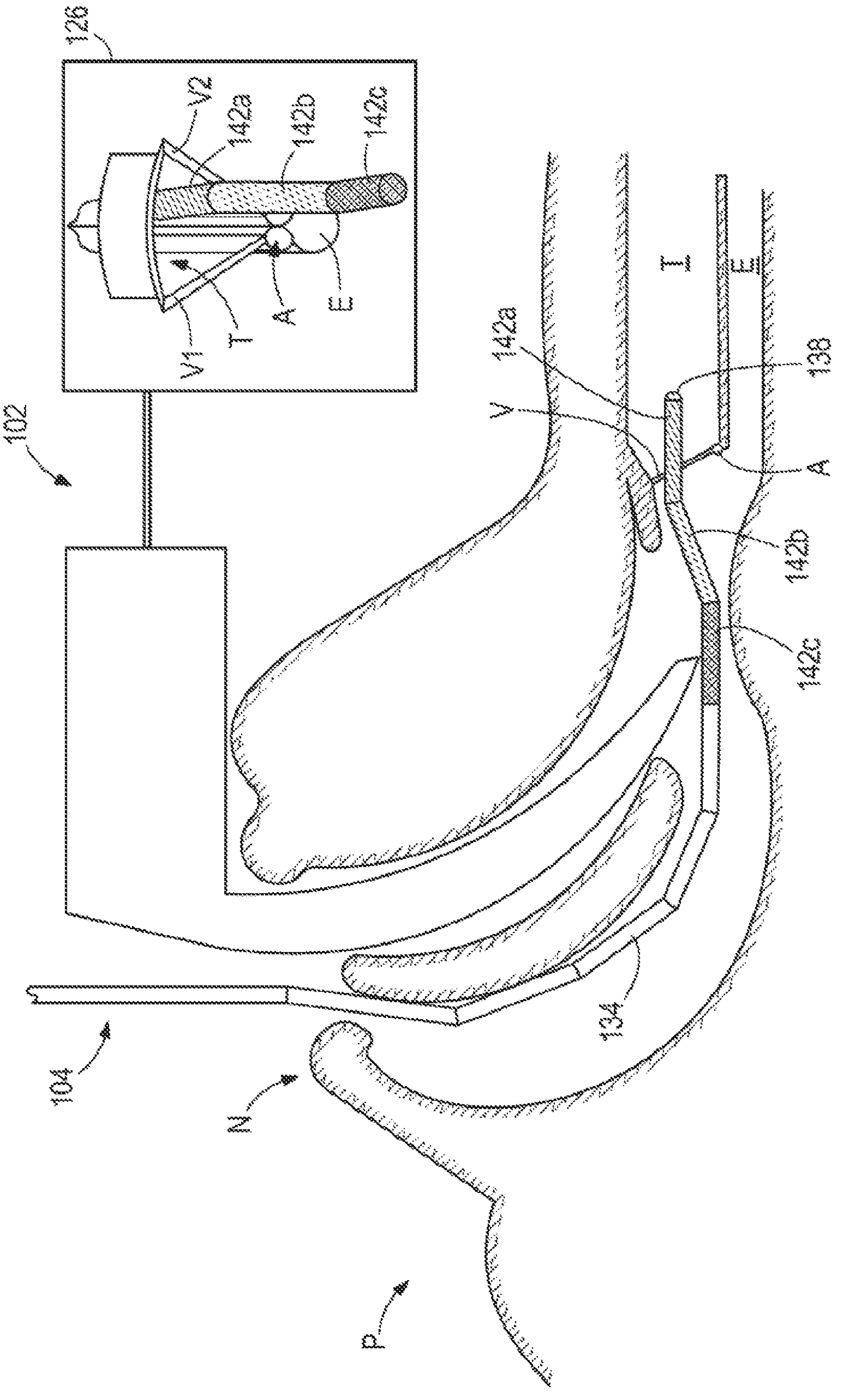

FIG. 7 illustrates a cross-sectional view of a patient P during an intubation procedure using an example tracheal intubation system that supports systems, devices, and techniques for positioning tubes in accordance with examples as disclosed herein. The tip 138 of the articulating stylet 104 is advanced into the trachea T of the patient P. The screen 126 shows that the first depth assessment band 142*a* is adjacent to the vocal cords V (e.g., the glottis of the patient). Accordingly, a caregiver may determine that the tip 138 needs to be advanced further into the trachea T by comparing the position of the depth assessment bands 142 with the anatomical structure of the patient (e.g., the vocal cords V).

Figure 8:
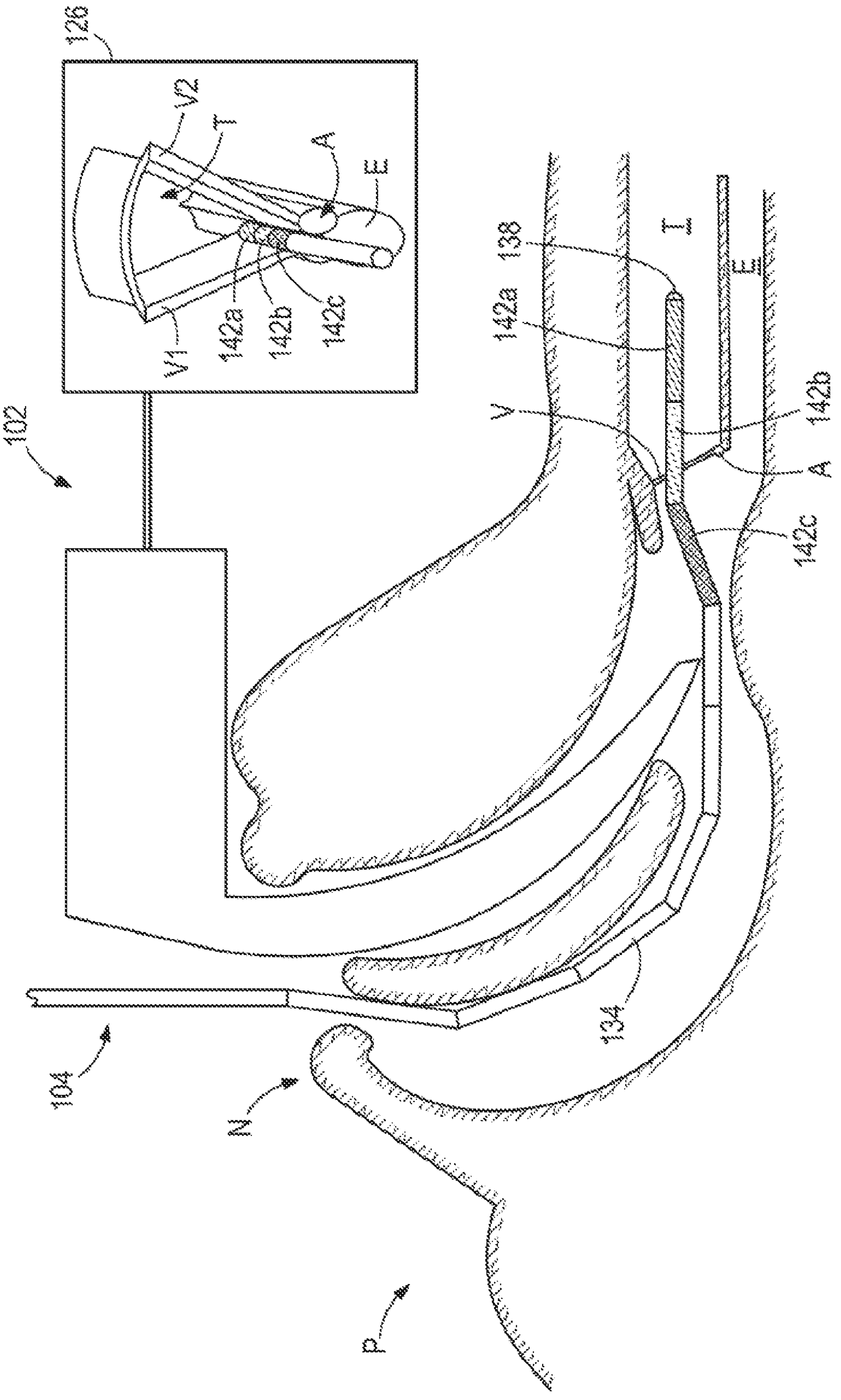

FIG. 8 illustrates a cross-sectional view of a patient P during an intubation procedure using an example tracheal intubation system that supports systems, devices, and techniques for positioning tubes in accordance with examples as disclosed herein. The tip 138 of the articulating stylet 104 is advanced further into the trachea T of the patient P as compared to FIG. 7. The screen 126 shows that the second depth assessment band 142*b* is now adjacent to the vocal cords V. Accordingly, a caregiver may determine that the tip 138 is properly positioned and it is not to be advanced further into the trachea T.

Figure 9:
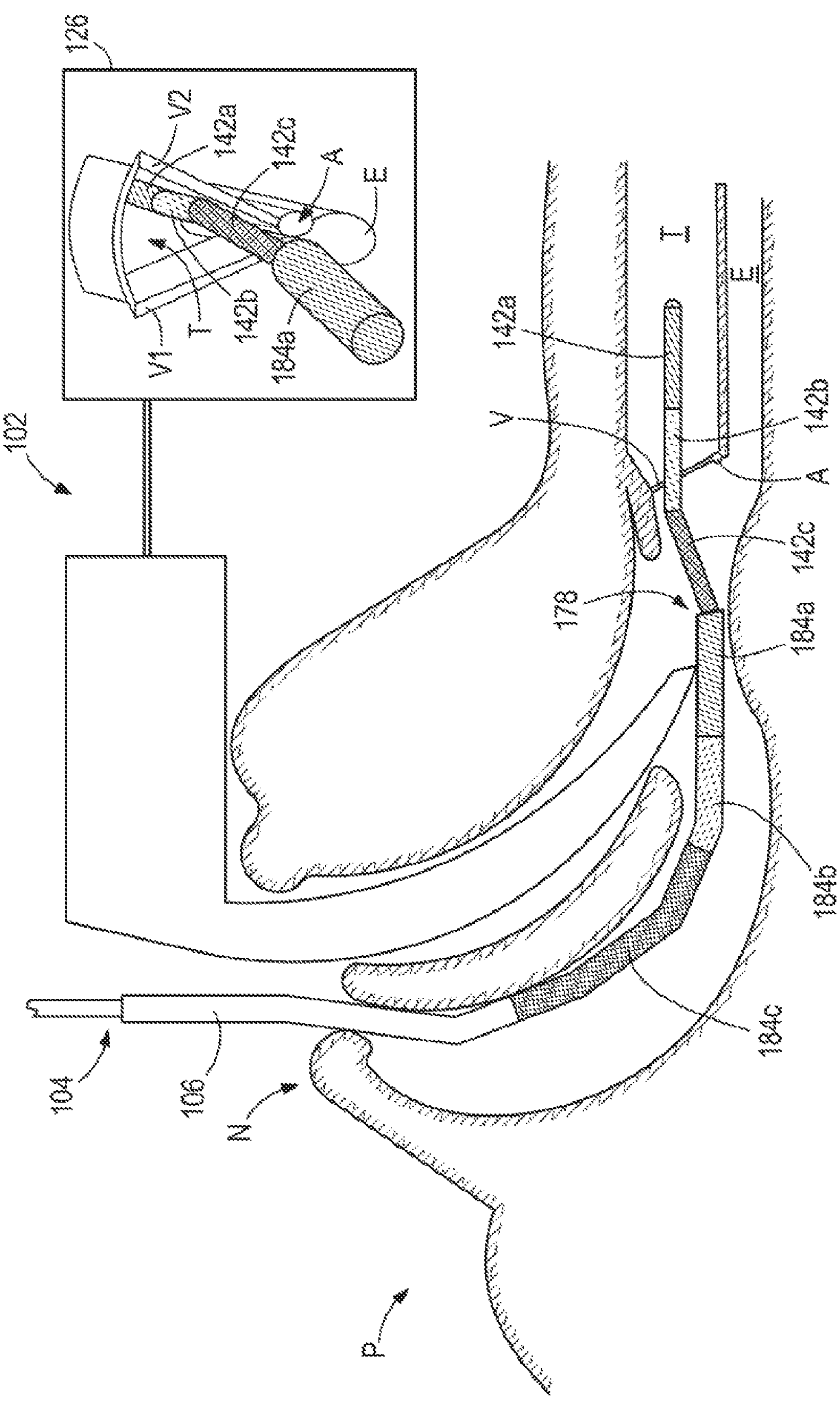

FIG. 9 illustrates a cross-sectional view of a patient P during an intubation procedure using an example tracheal intubation system that supports systems, devices, and techniques for positioning tubes in accordance with examples as disclosed herein. The tip 138 of the articulating stylet 104 may be properly positioned in the trachea T of the patient P. The endotracheal tube 106 has been advanced over the shaft 134 of the articulating stylet 104. The endotracheal tube 106 is guided by the articulating stylet 104 through the nose N of the patient P and into the pharynx of the patient P. In some cases, the endotracheal tube 106 may include one or more depth assessment bands 184. The first end 178 and the first depth assessment band 184*a* of endotracheal tube 106 are visible on the screen 126.

Figure 10:
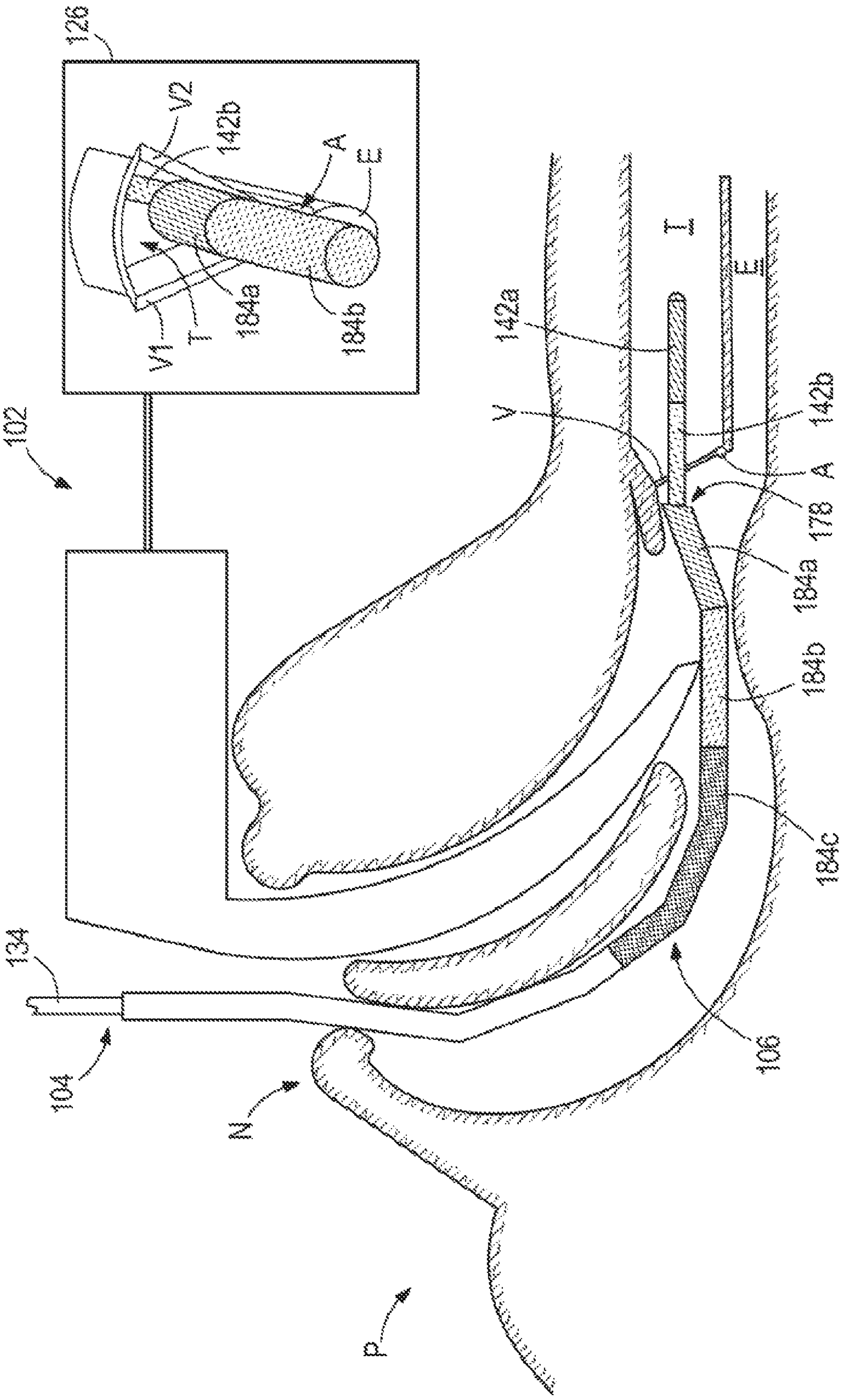

FIG. 10 illustrates a cross-sectional view of a patient P during an intubation procedure using an example tracheal intubation system that supports systems, devices, and techniques for positioning tubes in accordance with examples as disclosed herein. The tip 138 of the articulating stylet 104 is properly positioned in the trachea T of the patient P. The endotracheal tube 106 has been advanced further along shaft 134 of the articulating stylet 104 as compared to FIG. 9. The endotracheal tube 106 is guided into the trachea T of the patient P by the articulating stylet 104. The screen 126 displays that the first end 178 of endotracheal tube 106 has not yet reached the vocal cords V. Both the first depth assessment band 184*a* and the second depth assessment band 184*b* are visible on screen 125. But neither the first depth assessment band 184*a* nor the second depth assessment band 184*b* are adjacent to the vocal cords V yet. Accordingly, the caregiver may determine that the first end 178 of the endotracheal tube 106 needs to be advanced further to enter the trachea T of the patient P.

Figure 11:
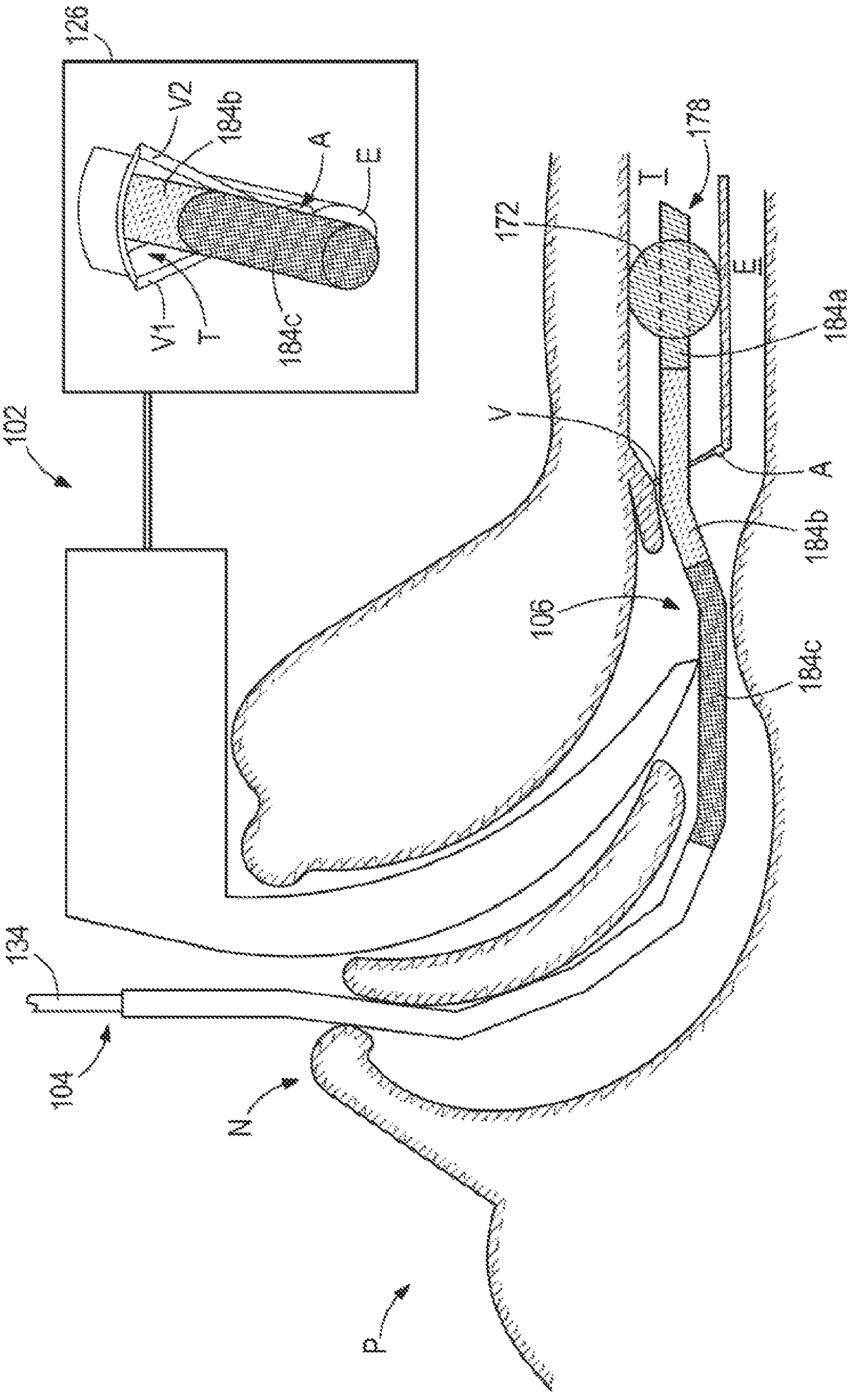

FIG. 11 illustrates a cross-sectional view of a patient P during an intubation procedure using an example tracheal intubation system that supports systems, devices, and techniques for positioning tubes in accordance with examples as disclosed herein. The endotracheal tube 106 has been advanced further along shaft 134 of the articulating stylet 104 as compared to FIG. 10. The screen 126 displays that the endotracheal tube 106 has entered the trachea T. Additionally, screen 126 displays that the second depth assessment band 184*b* is adjacent to the vocal cords V. Accordingly, a caretaker may determine that the endotracheal tube 106 has been guided into the trachea T of the patient P and has been properly positioned therein. If instead the first depth assessment band 184*a* were adjacent to the vocal cords V, a caregiver may determine that the endotracheal tube 106 needs to be advanced further into the trachea T of the patient P. Conversely, if instead the third depth assessment band 184*c* were adjacent to the vocal cords V, the caregiver might determine that the endotracheal tube 106 was advanced too far into the trachea T of the patient P. Once the endotracheal tube 106 is properly positioned, the cuff 172 is inflated to seal the trachea T and secure the endotracheal tube 106 in position.

Figure 12:
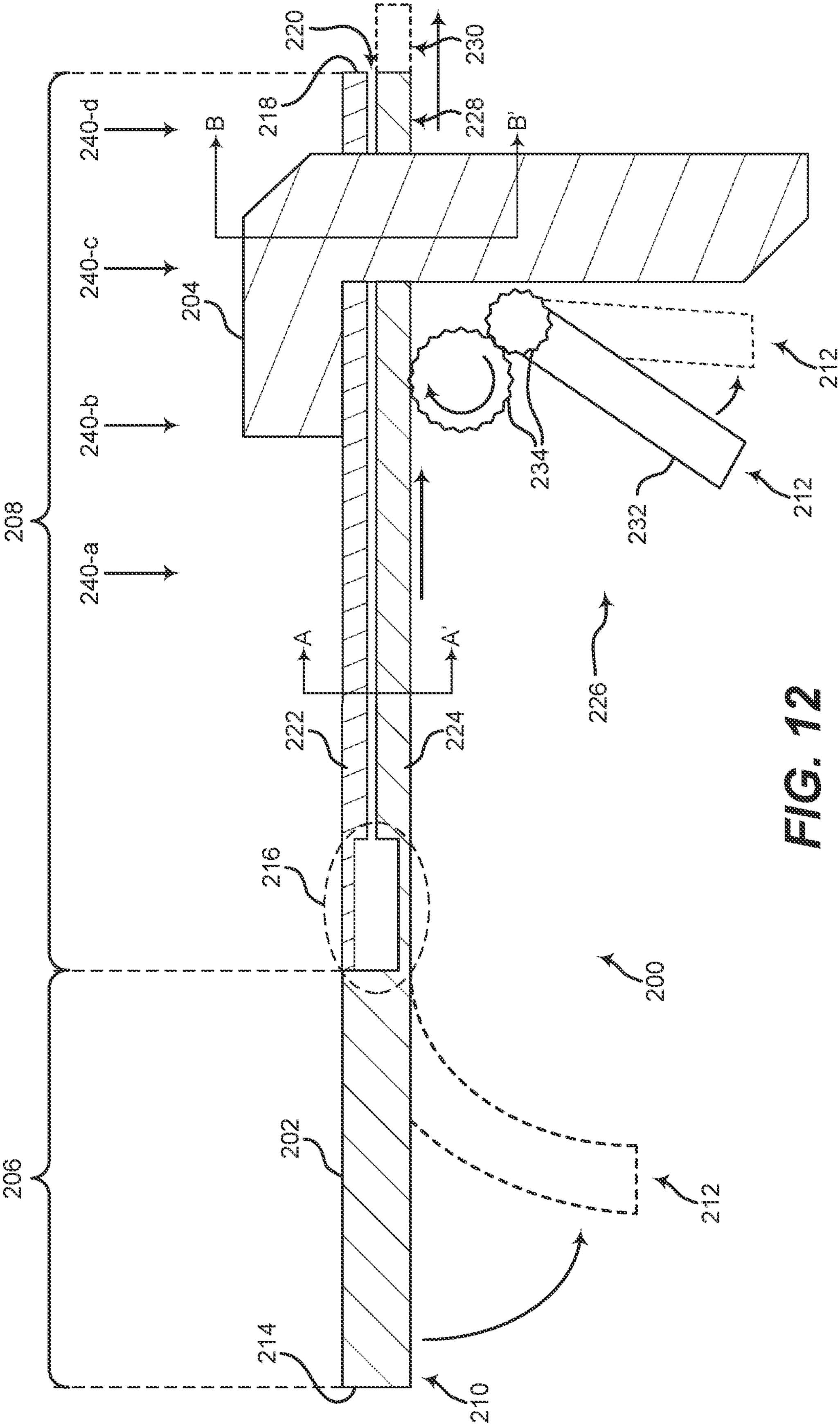
FIG. 12 illustrates a cross-sectional view of a tracheal intubation system that supports systems, devices, and techniques for positioning tubes in accordance with examples as disclosed herein.

FIG. 12 illustrates a cross-sectional view of a tracheal intubation system 200 that supports systems, devices, and techniques for positioning tubes in accordance with examples as disclosed herein. The tracheal intubation system 200 may include a stylet 202 configured to position a tube in an airway of a patient and a handle 204 configured to be secured in a fixed position relative to the stylet 202 and to cause a portion of the stylet 202 to move from a first position to a second position. The tracheal intubation system 200 may be an example of the intubation systems described with reference to FIGS. 1-11. The stylet may be an example of the stylets described with reference to FIGS. 1-11. The handle may be an example of the handles described with reference to FIGS. 1-11.

During some medical procedures or medical conditions, a patient may have challenges breathing. In such circumstances, a caregiver may insert a tube into the throat and the windpipe of the patient to make it easier to get air into and out of the lungs of the patient. The tube may be coupled with a ventilator that is configured to pump air into and out of the lungs of the patient.

A patient's vocal cords and the space between them form the entrance to the trachea. Collectively, these structures are also known as the glottis. The glottis is visible from and may be accessed through the pharynx. The pharynx is the portion of the upper airway that is located behind the patient's mouth and below the patient's nasal cavity. The mouth and the nasal cavity meet in the pharynx. Additionally, the esophagus and the glottis may be accessed through the pharynx. During the intubation process, an endotracheal tube should be carefully advanced through the patient's pharynx and placed through the vocal cords into the trachea.

The intubation process may interfere with the patient's ability to breathe and thus deliver oxygen to the body independently. If the patient is without oxygen for more than two or three minutes, tissue injury may occur, which can lead to death or permanent brain damage. Accordingly, the intubation process should be performed quickly and accurately.

The process of positioning the tube in the windpipe of the patient may be referred to as intubation. During an intubation procedure, a stylet or guide may be used by a caregiver to position the tube in a desirable location. The process of inserting the stylet into the patient or the resulting position of the tube may cause damage or trauma to the patient if incorrect. For example, the anatomy of a trachea is often not entirely straight and there may be curves in the anatomy of the patient. When navigating those curves, the stylet may impact other parts of the patient's throat. In other examples, if the tube is positioned too deeply into the windpipe of the patient it may cause unnecessary trauma or damage. In yet other examples if the tube is positioned too shallowly in the windpipe of the patient it may reduce its effectiveness.

Systems, devices, and techniques are described to position a tube in the trachea of the patient that reduces damage or trauma to the patient, as compared with other systems, devices, and techniques. The tracheal intubation system 200 may include a stylet 202 configured to position a tube in the trachea of the patient. The stylet 202 may include an articulating segment 206 and a support segment 208. The articulating segment 206 may be configured to move between a first position 210 and a second position 212 in response to input received by the support segment 208. The articulation or movement of the articulating segment 206 may be controllable by a caregiver to reduce collisions between the stylet 202 and the anatomy of the patient during the intubation process and thereby reduce trauma or damage. For example, in response to an input received, the articulating segment 206 may bend or move to a different position, allowing the stylet 202 to then be advanced further into the airway of the patient with a reduced risk of collisions with the anatomy of the patient, as described in more detail with reference to FIGS. 5-11.

The articulating segment 206 may be configured to move between the first position 210 and the second position 212. The first position 210 may include a first curve and the second position 212 may include a second curve. In an illustrative example, the first curve of the first position 210 may be having no curve and the second curve may be a curve downwards. In some cases, the first curve may be a curve upwards and the second curve may be a curve downwards or the second curve may be an example of no curve. Any combination of curves (or lack thereof) for the first position 210 and the second position 212 are possible. In some examples, additionally, the first position 210 or the second position 212 (or both) may include two or more curves. In some examples those two curves may be opposing curves that have different concavities. An example of a stylet with two opposing curves with different concavities may create an s-curve in the articulating segment 206.

The movement of the articulating segment 206 of the stylet 202 may be caused by a variety of mechanisms and interactions. The articulating segment 206 of the stylet 202 may extend from a distal tip 214 of the stylet 202 and a joint 216. The distal tip 214 of the stylet 202 may be configured to be inserted into the patient during an intubation procedure.

The support segment 208 of the stylet 202 may extend between the joint 216 and a proximal tip 218 of the stylet that may be configured to be outside of the patient during an intubation procedure. The support segment 208 may be configured to cause the articulating segment 206 to move between the first position 210 and the second position 212.

In some examples, the support segment 208 may include a longitudinal split 220 that divides the support segment 208 into a first portion 222 configured to be secured in a fixed position relative to the handle 204 and a second portion 224 configured to be moveable relative to the first portion 222 and to the handle 204. If one portion of the support segment 208 (e.g., the first portion 222) is held in a fixed position and another portion of the support segment 208 (e.g., the second portion 224) is moved, it may cause the articulating segment 206 to move. When combined with the handle 204, the motion of the support segment 208 may be controlled in such a way to cause predictable (and desirable) motion in the articulating segment 206. In such cases, movement of the second portion 224 of the support segment 208 may be configured to cause the articulating segment 206 to move between the first position 210 and the second position 212. Moving the articulating segment 206 between the first position 210 and the second position 212 may allow a caregiver to control a curve or shape of the stylet 202 anywhere between the first position 210 and the second position 212. Having the ability to shape the stylet 202 in a range of positions between the first position 210 and the second position 212 may allow the stylet 202 to accommodate the specific anatomy of the patient and thereby reduce trauma or damage that can occur as part of an intubation procedure.

The handle 204 may be configured to be secured in a fixed position relative to the stylet 202 and cause the articulating segment 206 of the stylet 202 to move between the first position 210 and the second position 212. In some cases, the first portion 222 of the support segment 208 may be secured in a fixed position relative to the handle 204 and the second portion 224 of the support segment 208 may be coupled with the handle 204 and may be moveable relative to the handle 204. In such cases, moving the second portion 224 and holding the first portion 222 in a relatively fixed position, may cause the articulating segment 206 to move between the first position 210 and the second position 212.

The handle 204 may include an actuator 226 configured to cause the second portion 224 to move between a first position 228 and a second position 230, which in turn may cause the articulating segment 206 to move between the first position 210 and the second position 212. The actuator 226 may be configured to receive an input from a user or caregiver and then apply a force to the second portion 224 of the support segment 208. In some cases, the actuator 226 may include a trigger 232 and one or more disks 234. The trigger 232 may move between a first position 236 and a second position 238 in response to an input from a user. The movement of the trigger 232 may cause rotational movement of the one or more disks 234. The rotational movement of the one or more disks 234 may cause linear movement of the second portion 224 between the first position 228 and the second position 230, which may cause the articulating segment 206 to bend between the first position 210 and the second position 212. In some examples, the second portion 224 may include a toothed or grooved track that interacts with one or more teeth of at least one of the disks 234. In some examples, the second portion 224 may be a surface configured to interact with the disk 234 using friction. In some cases, the actuator 226 may be example of a button, a slide, a knob that rotates, or any other structure (or combination of structures) that can translate input from a user or caregiver into linear movement of the second portion 224.

The handle 204 may configured to couple with the stylet 202 in a plurality of different longitudinal positions 240 along the length of the stylet 202. Examples of longitudinal positions of the handle 204 along the stylet 202 are shown with longitudinal position 240-*a*, longitudinal position 240-*b*, longitudinal position 240-*c* (which is the illustrated position of the handle 204), and longitudinal position 240-*d*. In some cases, however, any longitudinal position along the stylet 202 is possible.

The handle 204 may configured to couple with the stylet 202 in a plurality of different rotations positions around the stylet 202. The illustrated rotations position shows the handle 204 being in-line with the bend of the articulating segment 206. In some cases, the handle 204 may be coupled in a rotational position such that the bend of the articulating segment 206 may not be in-line with the handle 204. Any rotational position along the stylet 202 is possible. In some cases, the first portion 222 may be configured to move in response to movement of the actuator 226 and the second portion 224 may be secured in a fixed position. Any combination of longitudinal position and rotational position is possible.

In some cases, the stylet 202 may include a plurality of depth assessment bands (e.g., on the articulating segment 206, on the support segment, or a combination thereof). Each depth assessment band on the stylet 202 may be visually distinct from adjacent depth assessment bands. For example, a first depth assessment band located near the distal tip 214 may have a first visual representation configured to identify whether an insertion depth of the distal tip 214 is appropriate when positioned adjacent to an anatomical structure of a patient (e.g., the vocal chords or the glottis of the patient). In some cases, the first depth assessment band may indicate that the distal tip 214 has not been inserted to an appropriate insertion depth. In some cases, the first depth assessment band may indicate that the distal tip 214 has been inserted to an appropriate depth. In some cases, a first depth assessment band may indicate a zone of safety for the insertion depth of the distal tip 214 and a second depth assessment band may indicate a zone of warning for the insertion depth of the distal tip 214. In some cases, the stylet 202 may include three or more depth assessment bands indicating various zones of warning, zones of danger, and zones of safety. Each depth assessment band on the stylet 202 may have a visually distinct color or a visually distinct pattern or both from other depth assessment bands.

Figure 13:
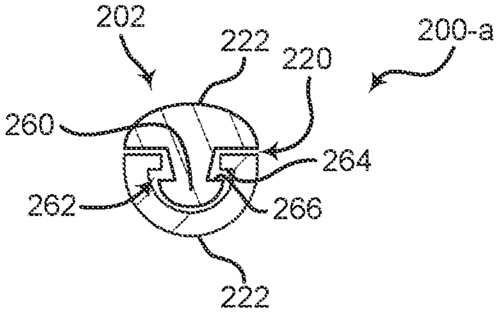
FIG. 13 illustrates a cross-sectional view of a tracheal intubation system taken along the line A-A' of FIG. 12 that supports systems, devices, and techniques for positioning tubes in accordance with examples as disclosed herein.

FIG. 13 illustrates a cross-sectional view of a tracheal intubation system 200-*a* taken along the line A-A' of FIG. 12 that supports systems, devices, and techniques for positioning tubes in accordance with examples as disclosed herein. The tracheal intubation system 200-*a* illustrates the support segment 208 of the stylet 202, including the first portion 222 and the second portion 224 separated by a longitudinal split 220.

When causing movement of one of the portions (e.g., the first portion 222 or the second portion 224), such movement may cause unintended movement from side-to-side instead of being lateral movement, in some cases. Structures may be used to guide the movement of the first portion 222 relative to the second portion 224.

In some cases, the first portion 222 may include a surface that forms a tongue 260 and the second portion 224 may include a surface that forms a groove 262. The tongue 260 may be configured to be inserted into the groove 262 and thereby guide the movement of the first portion 222 relative to the second portion 224. In some examples, the surface of the first portion 222 may form a first ledge 264 and the surface of the second portion 224 may form a second ledge 266. The first ledge 264 and the second ledge 266 may be configured to secure the tongue 260 in the groove 262 and thereby guide the movement of the portions 222, 224, relative to each other. In some examples, the tongue 260 and groove 262 may be configured to keep the first portion 222 together with the second portion 224 by mitigating a likelihood of separation in a first direction (e.g., away from each other), mitigating a likelihood of separate in a second direction (e.g., sliding off one other), and facilitate linear movement (e.g., into and out of the sheet as illustrated in FIG. 13). In some cases, the first portion 222 may include the groove 262 and the second portion 224 may include the tongue 260. Other structures for guiding the movement of the first portion 222 relative to the second portion 224 may be used.

Figure 14:
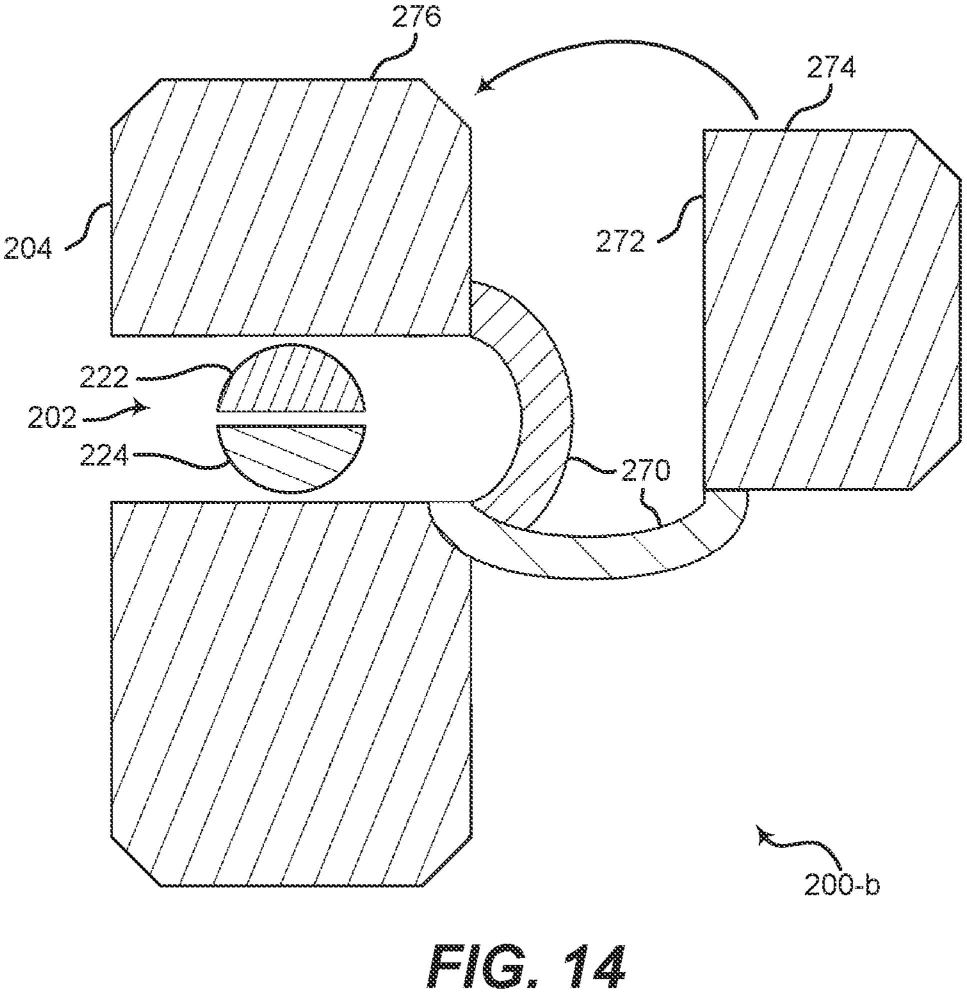
FIG. 14 illustrates a cross-sectional view of a tracheal intubation system taken along the line B-B' of FIG. 12 that supports systems, devices, and techniques for positioning tubes in accordance with examples as disclosed herein.

In some examples, the stylet may include a sleeve (not shown) that wraps around the first portion 222 and the second portion 224 and that is configured to mitigate a likelihood of separation in a first direction (e.g., away from each other), mitigate a likelihood of separate in a second direction (e.g., sliding off one other), and facilitate linear movement (e.g., into and out of the sheet as illustrated in FIG. 13). In such examples, the stylet 202 may not include a tongue and groove, but instead may include a straight along the length of the support segment 208 (e.g., as shown in FIG. 14). In some cases, the sleeve may extend at least a portion of the support segment 208 of the stylet 202. In some cases, a plurality of sleeves may be used to keep the first portion 222 and the second portion 224 from separating. In such cases, the different sleeves may be positioned in positions along the length of the stylet 202 and each sleeve may have a different length.

FIG. 14 illustrates a cross-sectional view of a tracheal intubation system 200-*b* taken along the line B-B' of FIG. 12 that supports systems, devices, and techniques for positioning tubes in accordance with examples as disclosed herein. The tracheal intubation system 200-*b* illustrates the handle 204 interacting with the stylet 202. The handle 204 may include a release mechanism 270 configured to selectively couple with the handle 204 with the stylet 202. The release mechanism 270 may be configured to move a portion 272 of the handle 204 between a first position 274 that is open and a second position 276 that couples the handle 204 with the first portion 222 and the second portion 224 of the stylet. The release mechanism 270 may be configured such that the handle 204 may be positionable or repositionable in any longitudinal position or rotational position along the stylet 202. A user or a caregiver may actuate the release mechanism 270 to either secure stylet 202 relative to the handle 204 or to release the stylet 202 relative to the handle 204.

Figure 15:
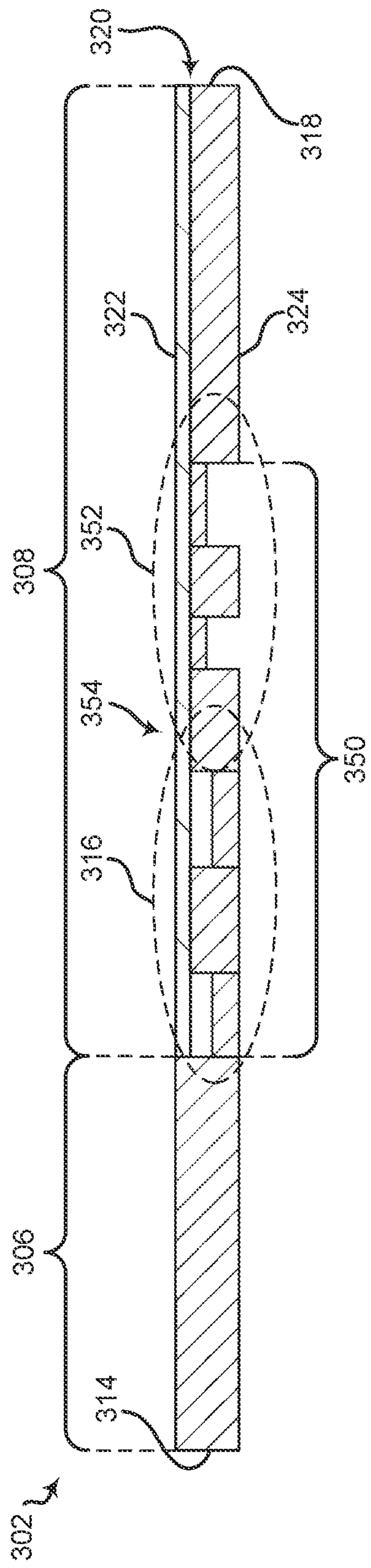
FIG. 15 illustrates a cross-sectional view of a stylet that supports systems, devices, and techniques for positioning tubes in accordance with examples as disclosed herein.

FIG. 15 illustrates a cross-sectional view of a stylet 302 that supports systems, devices, and techniques for positioning tubes in accordance with examples as disclosed herein. The stylet 302 may be an example of the stylet 202 described with reference to FIGS. 12-14 and similar named and numbered elements may have similar features, functions, and relationships. As such, where applicable, the description of FIGS. 12-14 may be incorporated into the description of FIG. 15 to avoid some repetition.

The stylet 302 may be configured to position a tube in an airway of a patient and may be configured to move from a first position to a second position. The articulating segment 306 may be configured to move between the first position 410 and the second position 414, as shown and described in more detail with reference to FIG. 16. The movement of the articulating segment 306 of the stylet 302 may be caused by a variety of mechanisms and interactions. The articulating segment 306 of the stylet 302 may extend from a distal tip 314 of the stylet 302 and a first joint 316. The distal tip 314 of the stylet 302 may be configured to be inserted into the patient during an intubation procedure.

The support segment 308 of the stylet 302 may extend between the first joint 316 and a proximal tip 318 of the stylet that may be configured to be outside of the patient during an intubation procedure. The support segment 308 may be configured to cause the articulating segment 306 to move between the first position 310 and the second position 312.

In some examples, the support segment 308 may include a longitudinal split 320 that divides the support segment 308 into a first portion 322 configured to be secured in a fixed position relative to the articulating segment 306 and a second portion 324 configured to be moveable relative to the first portion 322 and to the articulating segment 306. If one portion of the support segment 308 (e.g., the first portion 322) is held in a fixed position and another portion of the support segment 308 (e.g., the second portion 324) is moved, it may cause the articulating segment 306 to move. In such cases, movement of the second portion 324 of the support segment 308 may be configured to cause the articulating segment 306 to move between the first position 410 and the second position 414 along with causing a sub-segment 350 of the support segment 308 to move between a first position 412 and a second position 416. Moving the articulating segment 306 between the first position 412 and the second position 416 may allow a caregiver to control a curve or shape of the stylet 302 anywhere between the first position 412 and the second position 416. Having the ability to shape the stylet 302 in a range of positions between the first position 412 and the second position 416 may allow the stylet 302 to accommodate the specific anatomy of the patient and thereby reduce trauma or damage that can occur as part of an intubation procedure. Moving the support segment 308 between the first position 414 and the second position 418 may allow a caregiver to control a curve or shape of the stylet 302 anywhere between the first position 414 and the second position 418. Having the ability to shape the stylet 302 in a range of positions between the first position 414 and the second position 418 may allow the stylet 302 to accommodate the specific anatomy of the patient and thereby reduce trauma or damage that can occur as part of an intubation procedure.

The support segment 308 may include a second joint 352 configured to cause more complex curves or bends in the stylet 302 as compared with the stylet 202. For example, a double joint stylet may be configured to allow multiple curves (e.g., an s-curve structure) when bending the stylet 302. In some cases, a structure 354 may couple the first joint 316 with the second joint 352. In some examples, the structure 354 may be an example of a cable or some other rigid or semi-rigid structure that places constraints on movement of the first portion 322 relative to movement of the second portion 324 (or vice-versa). When the second portion 324 (or the first portion 322) is moved, the structure 354 constrain the movement of the stylet 302 in the sub-segment 350. In such examples, the structure 354 may be configured to cause the sub-segment 350 to move between the first position 412 and the second position 416. Additional details about the movement of the stylet 302 is described with reference to FIG. 16.

Figure 16:
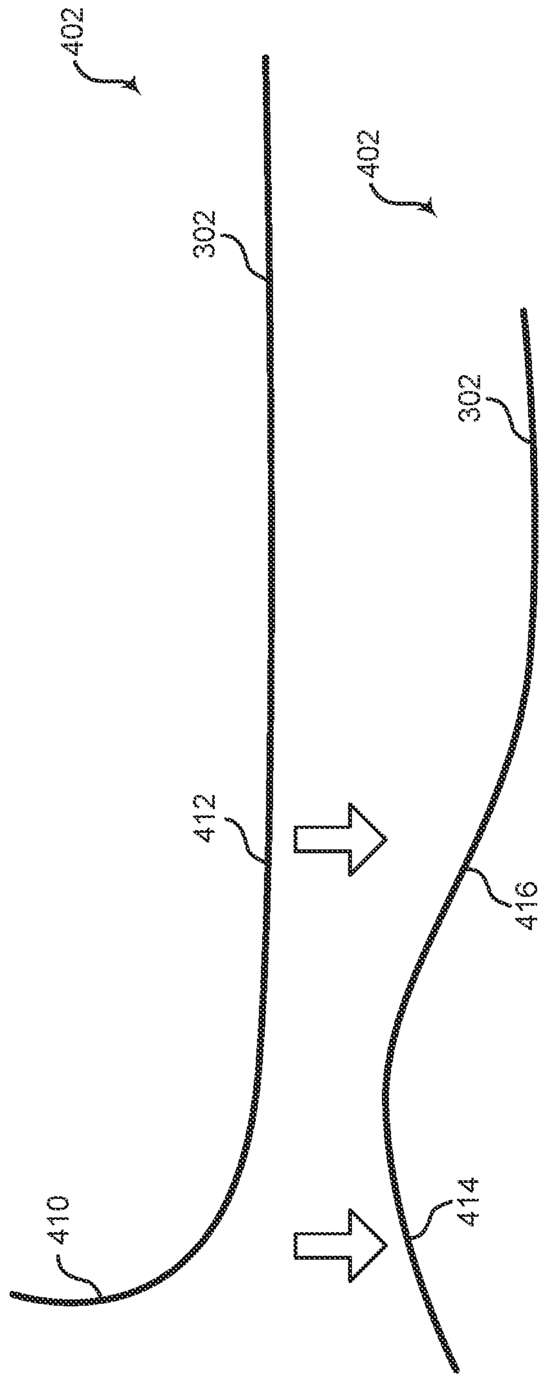
FIG. 16 illustrates an example of positions of a stylet that supports systems, devices, and techniques for positioning tubes in accordance with examples as disclosed herein.

FIG. 16 illustrates an example of positions of a stylet 302 that supports systems, devices, and techniques for positioning tubes in accordance with examples as disclosed herein. The stylet 302 may have a first position 402 that represents when the stylet 302 is relaxed and a second position 404 that represents when the stylet 302 may be under tension from an input of a user or caregiver cause the stylet 302 to bend.

The first position 402 may include a first position 410 of the articulating segment 306 and includes a first curve and a first position 412 of the sub-segment 350 of the support segment 308 that includes a second curve. In the illustrative example, the first position 402 includes one continuous curve that has the same concavity (e.g., based on the first curve and the second curve).

The second position 404 may include a second position 414 of the articulating segment 306 that includes a third curve and a second position 416 of the sub-segment 350 of the support segment 308 that includes a fourth curve. In the illustrative example, the second position 404 includes one continuous curve that has two opposing curves that have different concavities (e.g., an s-curve structure). The third curve of the articulating segment 306 may have a first concavity that is downward in the illustrative example and the fourth curve of the sub-segment 350 may have a second concavity that is upwards in the illustrative example.

Figure 17:
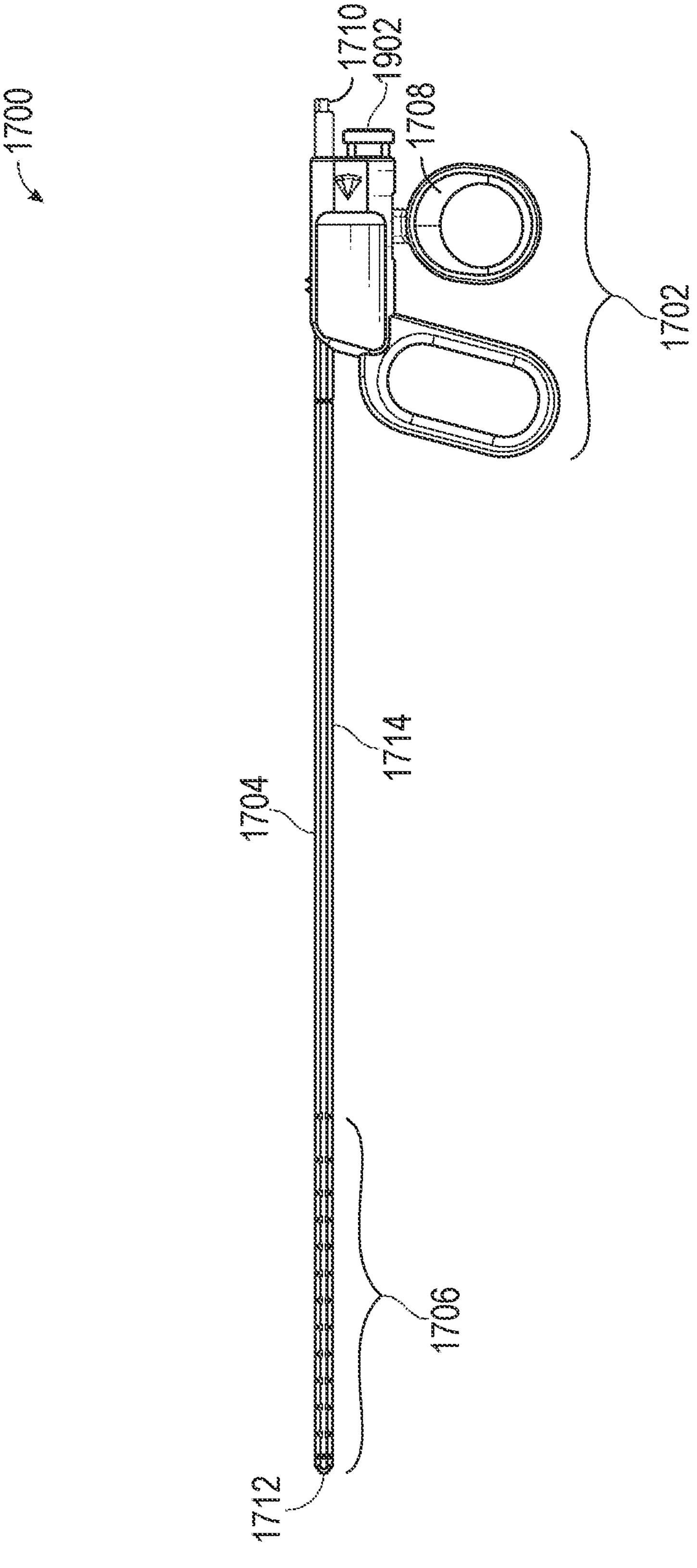
FIG. 17 illustrates an articulating endotracheal tube introducer in accordance with examples as disclosed herein.

Turning to FIG. 17, aspects of the present disclosure may include an articulating endotracheal tube introducer 1700 which may be used with any laryngoscope. The features of the articulating endotracheal tube introducer 1700 may be configured such that the introducer 1700 may be used with a single hand. The articulating endotracheal tube introducer 1700 may include a handle assembly 1702 and a removeable shaft 1704. The handle assembly 1702 may be configured to control tip articulation of an articulating tip component 1706. In an embodiment, the shaft 1704 may be removed from the handle assembly 1702. However, the shaft 1704 may be permanently fixed to the handle assembly 1702. The articulating endotracheal tube introducer 1700 may include a flexible shaft 1704. The articulating endotracheal tube introducer 1700 may also include an articulating tip component 1706 located at an end of the shaft 1704. The articulating tip component 1706 may have an asymmetric bend. However, in alternate embodiments, the articulating tip component 1706 may have a symmetric bend, or any suitable bend. The flexible shaft 1704 may include a support component extending between the joint of the shaft 1704 and a proximal tip of the shaft 1704.

In an embodiment, the introducer 1700 may include, or be in communication with, an endotracheal tube ("ETT"), which may be configured to fit over the shaft 1704. The introducer 1700 may also include, or be in communication with, a clothesline mechanism for control of the motion of the articulating tip component 1706 with a potential of crossing wire functionality. In an embodiment, the trigger 1708 may be configured to interact with a tip control mechanism. For example, when the shaft is loaded into the handle. In an embodiment, the articulating endotracheal tube introducer 1700 includes a single-handed operator release mechanism 1806.

Figure 18A:
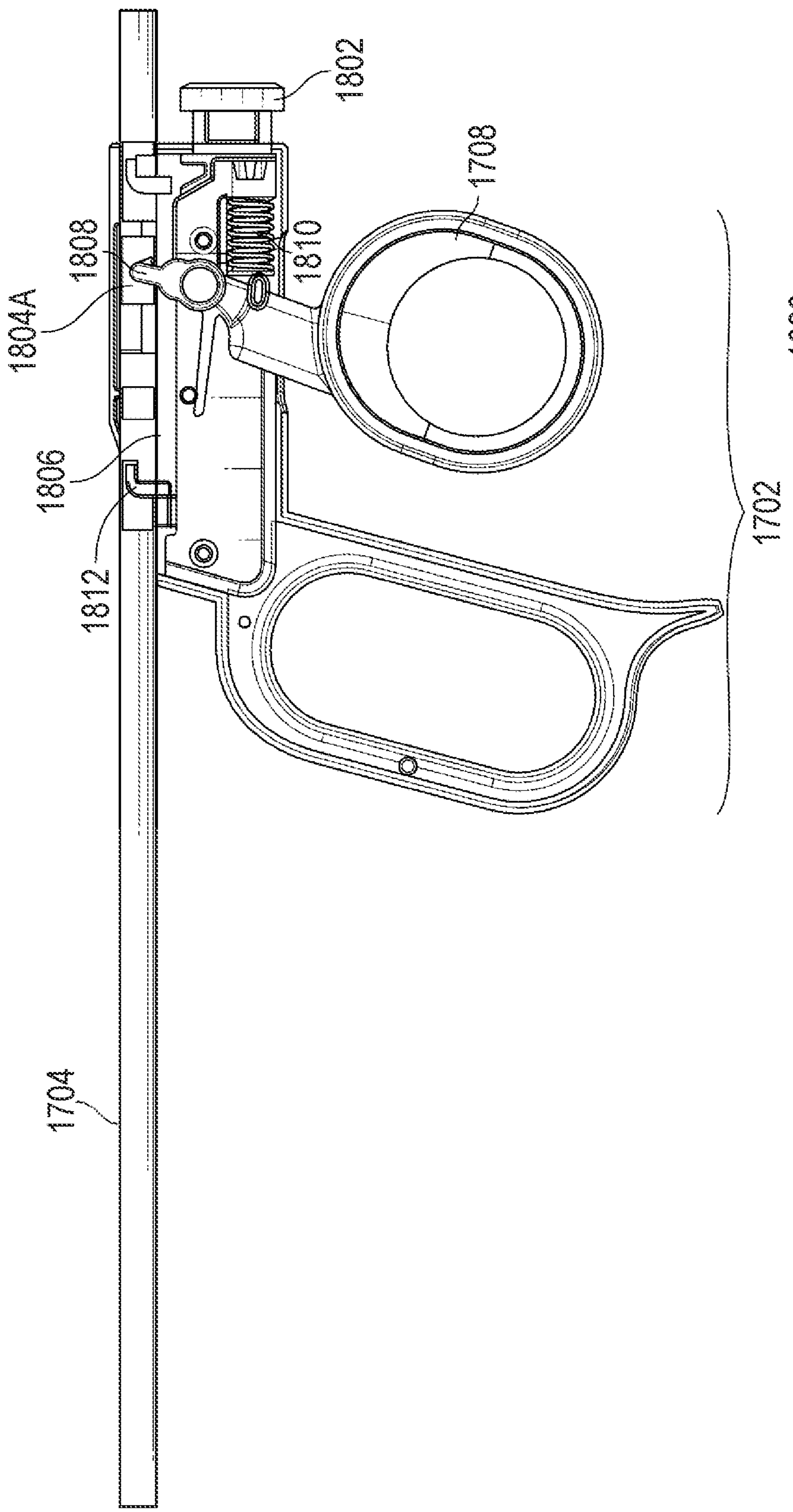
FIG. 18A shows a partial top-view of an articulating endotracheal tube introducer including a retention apparatus in accordance with examples as disclosed herein.
Figure 18B:
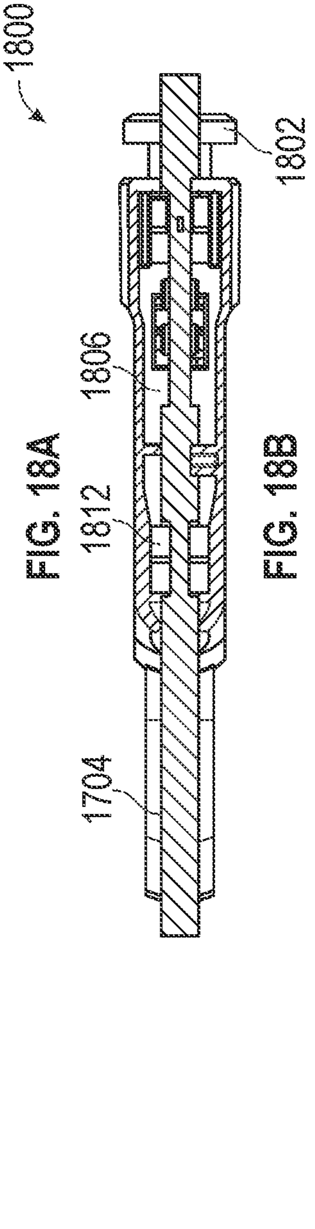
FIG. 18B shows a cutaway of an articulating endotracheal tube introducer in accordance with examples as disclosed herein.

FIG. 18 illustrates a cutaway view of the introducer 1700 according to various aspects of the present disclosure. In an embodiment, the introducer 1700 includes a release button 1802 and retention apparatus 1800. The retention apparatus 1800 may interact directly with the shaft 1704 in order to hold the shaft 1704 in place in the handle assembly 1702 in one position. The retention apparatus 1800 may release the shaft 1704 when the release button 1802 and retention apparatus 1800 are moved into a second position. In such an embodiment, the release button 1802 and retention apparatus 1800 are one piece. However, in an alternate embodiment, more than one piece may be used to accomplish release of the shaft 1704. In an embodiment, the retention apparatus 1800 interacts with the shaft 1704 via one or more grooves, holes, or ledges that allow retention of the shaft 1704 in one position and release of the shaft 1704 in a second position.

In an embodiment, the apparatus includes a reloadable shaft 1704 and/or a reloadable handle 1702. The introducer 1700 may be configured such that the shaft 1704 may be indexed for reloading or may include an indexed shaft. In an embodiment, the introducer 1700 may include a folding tail design. In such an embodiment, a tail portion component of the shaft 1704, located toward the proximal end of the shaft 1704, may be configured to fold toward the distal end of the shaft 1704. In one embodiment, the handle assembly 1702 may be positioned at an approximate mid-point of the shaft 1704. The ETT may be preloaded on the tail portion component of the shaft 1704. Portions of the introducer 1700 (for example, specifically the handle 1702) may include grooves and/or indentations that act as grips for a user's fingertips. The introducer 1700 may also include two finger loops. The introducer 1700 may be configured for thumb operation. In an embodiment, the introducer 1700 includes an atraumatic tip. The shaft 1704 may be flexible and may be configured to move the articulating tip component 1706. The introducer 1700 and/or components of the introducer 1700 may be indexed by a qualitative depth system. For example, the shaft 1704 may be gauged to one's vocal cords.

In an embodiment, any mechanism configured to control the articulating tip component 1706 may be arranged in such a way as to both: control the articulating tip component 1706 via an input and fit through the internal channel of an ETT so that the ETT can pass over the entire shaft 1704 and mechanism from one end of the shaft 1704 to the other in order to place the ETT into the trachea over the introducer. The mechanism may be located within the shaft 1704. In an embodiment, a sequence may be as follows: (1) video laryngoscope 102 is placed into the patient's mouth until a view of the glottis is obtained; (2) the articulating introducer 1700 is griped in the hand or fingers or by a surgical robot in order to control the entire shaft 1704 orientation and articulating tip component 1706 articulation; (3) the articulating introducer 1700 is placed tip first into the mouth until its articulating tip component 1706 is in the visual field of the video laryngoscope 102; (4) an input is transmitted to the mechanism controlling tip articulation either directly or via a releasable handle; (5) the articulating tip component 1706 is articulated while advancing the introducer 1700 in order to navigate the articulating tip component 1706 and shaft 1704 into the trachea; (6) once the introducer 1700 is placed into the trachea, the depth of the introducer 1700 in the trachea can be assessed by viewing visually distinct qualitative depth zones on the leading shaft 1704 of the introducer 1700 and by comparing these different zones to the vocal cords (glottis) of the patient; (7) once the introducer 1700 is well placed in the trachea, the removable handle 1702 (if present) may be removed from the introducer shaft 1704 in such a way as to remove the handle 1702 and leave the introducer shaft 1704 well placed into the trachea; (8) an ETT may then be advanced over the introducer 1700 in such a way that the introducer 1700 passes through the internal channel of the ETT, over the tip articulation controlling mechanism, and into the trachea; (9) once the ETT is passed over the introducer 1700 and into the trachea, the introducer 1700 can be removed via the back of the ETT, leaving the ETT in place in the trachea; and (10) the ETT may then be connected to a ventilatory device and the patients lungs can be ventilated. In alternate embodiments, such a sequence may include the aforementioned steps in any order. The aforementioned sequence is a non-limiting example and may have alternate versions consistent with this disclosure.

In an embodiment, with the aforementioned steps in mind, the handle 1702 that is used to transmit inputs to the introducer shaft 1704 may be able to transmit inputs that control tip articulation in such a way as to: (1) translate any input from the handle 1702 into tip articulation; (2) allow the handle 1702 to be quickly and easily released from the shaft 1704 once transmission of said input is no longer needed for navigation into the trachea; and (3) fit through the central channel of an ETT from end to end (however, as a non-limiting example, not through the handle 1702).

In an embodiment, the shaft 1704 of the introducer 1700 may have a controllable articulating tip component 1706 that can provide active and precise navigation into the trachea, having a flexible shaft 1704 so that the shaft 1704 can easily conform to the airway as it follows the articulating tip component 1706 into the trachea. Further, there may be a system that allows the introducer tip depth relative to the trachea to be understood in real time.

Figure 19:
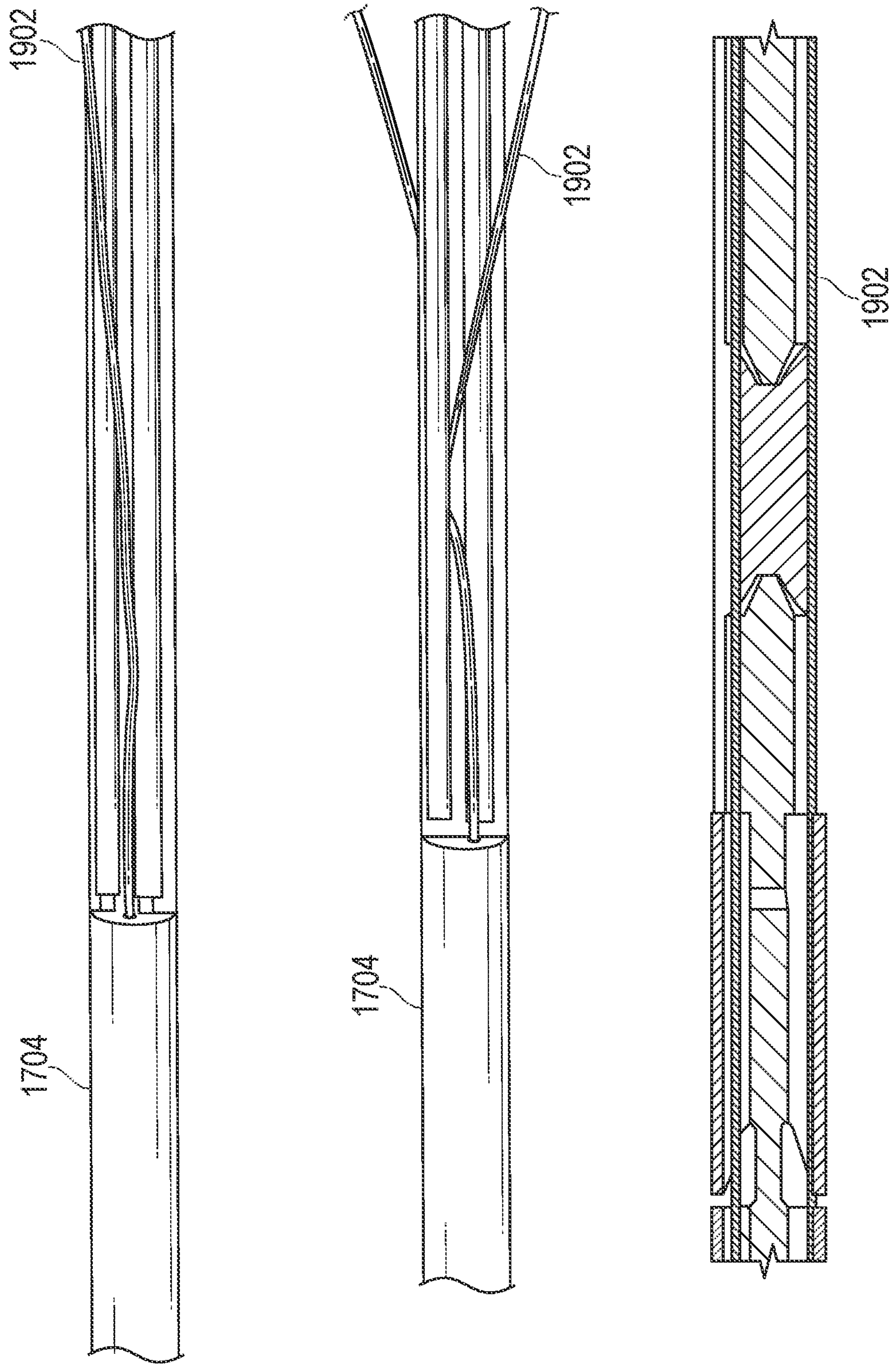
FIG. 19 illustrates one or more wires housed within a shaft in accordance with examples as disclosed herein.

As shown in FIG. 19, an aspect of the present disclosure may include an improved mechanism for introducer tip articulation that allows the articulating tip component 1706 and shaft 1704 to be dynamically articulated and shaped while in use and at the same time pass the central channel of an ETT. In an embodiment, the articulating introducer 1700 includes either a single wire 1902, which causes the articulating tip component 1706 to articulate, or contains two wires 1902 that push and pull simultaneously to cause the articulating tip component 1706 to articulate.

In an embodiment, the apparatus uses a single wire 1902, which may be attached to the articulating tip component 1706 of the introducer shaft 1704. The loop formed by this wire may then be placed around a post, or pulley more proximal in the shaft 1704. In such an embodiment, pulling on one section of the wire automatically relaxes the other section of wire causing the articulating tip component 1706 to deflect in a direction. The handle 1702 may interface with the wire 1902 in such a way as to be able to transmit an input in order to push or pull the wire 1902 causing the articulating tip component 1706 to deflect and at the same time be easily removed from the wire 1902 so that the introducer shaft 1704 may be passed from end to end through the channel of the ETT.

In another embodiment, a removable handle interface 1804 may include a pulley such that when an input is transmitted to the pulley, the pulley is caused to rotate, in turn causing the wire 1902 to be either pushed or pulled. The removable handle interface 1804 may slide along a rod when acted upon by the input. The input may be provided via the trigger 1708 as shown in FIG. 18A. In such an embodiment, the removable handle interface 1804 includes a groove which may be sized to accept a trigger actuator 1808. In an embodiment, the wire 1902 is fixed to the removable handle interface 1804. The removable handle interface 1804 may be set to a default position when the trigger 1708 is not being acted upon by a user. In such an embodiment, the handle 1702 may include a spring 1810 connected to the trigger 1708 such that, when the trigger 1708 is not being acted upon by a user, the spring 1810 is in an extended state.

However, these are two examples of how the removable handle 1702 may transmit a force to the wire 1902 in order to cause the articulating tip component 1706 to deflect. It is noted that other mechanisms and embodiments are consistent with this disclosure.

The wire 1902 may be made of any material capable of transmitting a force to the articulating tip component 1706 of the introducer 1700 in order to make the articulating tip component 1706 deflect.

In an embodiment, the handle 1702 may be operated with an operator's fingertips of one hand. However, in another embodiment, it may be operated with more than one hand, or even more than one operator. In one embodiment, the handle 1702 is designed for use in the right hand, however the introducer 1700 may be designed for the left hand or either hand as well.

In an embodiment, the handle 1702 may be easily released after the introducer 1700 is placed in the trachea. The introducer 1700 may be configured with a release mechanism 1806 that can be activated with a single digit of the operator's hand without the need to fully remove the hand that is operating the articulating handle 1702.

The release mechanism 1806 may include a button 1802, a lever, or a slide. However, in alternate embodiments, other release mechanisms are possible. In an embodiment, when a force is exerted on the button 1802, the force causes the release mechanism 1806 to slide toward a distal end of the introducer 1700. In such an embodiment, the motion of the release mechanism causes one or more mounts 1812 to disengage with the shaft 1704. The shaft 1704 may include one or more grooves to interface with the one or more mounts 1812. In an embodiment, the one or more mounts 1812 may be configured to product an audible "click" sound when engaging, or disengaging, with the shaft 1704. Such a sound may be achieved by adding a ridge to the shaft 1704 and/or one or more mounts 1812.

In an embodiment, the introducer 1700 includes one or more sensors. In an embodiment, a sensor integrated into the introducer 1700 may sense chemicals to understand the chemical aspects of the environment surrounding the introducer 1700. Non-limiting examples of chemicals that may be sensed may be: carbon dioxide, oxygen, hydrogen, and acid/base characteristics.

Temperature, friction, and force are other aspects of the physical environments that may be sensed. However, in further embodiments, other physical properties may be sensed as well.

Thus, the anatomy surrounding the introducer may be better understood and differentiated in order to better understand placement in the body. As a non-limiting example, sensing carbon dioxide may help understand if the introducer has entered the trachea or the esophagus.

These sensors may assist in aspects of navigation during access into an anatomic space or confirmation of proper placement in an anatomic space. For example, the space of interest may be the trachea. However, other anatomic spaces may be of interest for other procedures besides intubation.

Such procedures may be ventriculostomy, colonoscopy, placement of drains or catheters into various vascular, gastrointestinal, plural, genital, urological, neurological, optical, peritoneal, retroperitoneal, or pleural spaces.

In an embodiment, sensor inputs may then be transmitted to a human or machine for processing for either strategic or tactical use. This processed data may be stored for future use or used immediately.

Processed outputs may be used in real time to guide the operator or surgical robot in performing the procedure via producing signals that may be fed back in real time to the operator or machine controlling the laryngoscope 102, introducer 1700, or ETT. This system may be used for real patient care or for simulated patient care while training. In terms of training, this system of sensors, processors, and feedback may enhance the speed of training, the understanding of training, and assessment of the results of training.

In an embodiment, the introducer 1700 may include any of the following: introducer shaft 1704: distal shaft 1712, mid shaft 1714, proximal shaft 1710; flexible section between the mid shaft and distal shaft; at least one control wire 1902; removable handle 1702; handle control components to transmit inputs corresponding to tip articulation; release mechanism 1806; and depth management system.

The invention of the present disclosure may be used in the following non-limiting applications: intubation, ETT exchange, endovascular catheter placement, and drain placement.

In an embodiment, this invention allows for more precise articulating tip component 1706 control, and a way to control the articulating tip component 1706 with an actuator mechanism that can interface with the wire 1902 when loaded and easily release when removed. This may allow for smooth and precise device and tip articulation control when the handle 1702 is in place. Once the shaft 1704 is in the trachea, the handle 1702 may be removed in order to easily place the ETT over the shaft 1704 of the introducer 1700.

In an embodiment, the invention of the present disclosure may include the following steps: Step 1, visualize glottis; Step 2, apply inputs to the handle 1702 to both control the handle 1702 and introducer shaft 1704 in order to move the entire introducer 1700 and articulate the articulating tip component 1706 as needed to navigate the articulating tip component 1706 of the introducer 1700 to the glottis and into the trachea; Step 3, release the handle 1702 from the shaft 1704 using the release mechanism 1806; Step 4, remove handle 1702 from the shaft 1704 while leaving the shaft 1704 in place in the trachea; Step 5, advance the ETT over the proximal end 1710 of the introducer 1700 in such a way that the introducer 1700 passes through the central channel of the ETT; Step 6, advance the ETT over the introducer 1700 and place into the trachea until the desired ETT depth is achieved; and Step 7, remove introducer 1700 out the back of the ETT leaving the ETT in place in the trachea.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details to providing an understanding of the described techniques. These techniques, however, may be practiced without these specific details. In some instances, well-known structures and devices are shown in block diagram form to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

As used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

The description herein is provided to enable a person skilled in the art to make or use the disclosure. Various modifications to the disclosure will be apparent to those skilled in the art, and the generic principles defined herein may be applied to other variations without departing from the scope of the disclosure. Thus, the disclosure is not limited to the examples and designs described herein but is to be accorded the broadest scope consistent with the principles and novel features disclosed herein.

What is claimed is:

1. A tracheal intubation system, comprising:

a stylet configured to mount an endotracheal tube, the stylet including:

an articulating segment extending between a distal tip of the stylet and a joint of the stylet, the articulating segment configured to move relative to the joint;

a support segment extending between the joint of the stylet and a proximal tip of the stylet, the support segment configured to cause the articulating segment to move between a first position and a second position, wherein the support segment comprises a longitudinal split that divides the support segment into a first portion and a second portion, the first portion including a surface that forms a groove, and the second portion comprising a tongue configured to insert into the groove formed by the first portion; and a handle configured to couple with the support segment of the stylet and configured to cause at least a portion of the support segment to move to results in the articulating segment of the stylet moving.

2. The tracheal intubation system of claim 1, wherein one of the first portion and the second portion is a fixed portion configured to be secured in a fixed position relative to the handle and the other of the first portion and the second portion is a movable portion configured to be moveable relative to the fixed portion and to the handle.

3. The tracheal intubation system of claim 2, wherein the handle further includes an actuator configured to cause the movable portion of the support segment to move relative to the fixed portion in response to movement of the actuator.

4. The tracheal intubation system of claim 3, wherein the actuator further comprises:

a trigger configured to cause rotational movement in a disk in response to the trigger moving from a third position to a fourth position, wherein the disk is configured to cause linear movement of the movable portion of the support segment in response to the rotational movement of the disk, wherein the linear movement of the movable portion the second portion of the support segment is configured to cause the articulating segment to move between the first position and the second position.

5. The tracheal intubation system of claim 4, wherein the disk is configured to couple with a grooved track of the movable portion of the support segment.

6. The tracheal intubation system of claim 1, wherein the handle further includes:

a release mechanism configured to selectively couple the handle with the stylet.

7. The tracheal intubation system of claim 1, wherein the stylet further comprises:

a plurality of depth assessment bands located on the articulating segment, each depth assessment band visually distinct from an adjacent depth assessment band, a first depth assessment band located near the distal tip and having a first visual representation configured to whether an insertion depth of the distal tip is appropriate when positioned adjacent to an anatomical structure of a patient.

8. The tracheal intubation system of claim 7, wherein the anatomical structure of the patient is a vocal cord of the patient.

9. The tracheal intubation system of claim 1, wherein:

the first portion comprises a first ledge;

the second portion comprises a second ledge; and the first ledge and the second ledge configured to secure the tongue of the second portion in the groove formed by the first portion.

10. A stylet configured to mount an endotracheal tube, comprising:

an articulating segment extending between a distal tip of the stylet and a joint of the stylet, the articulating segment configured to move relative to the joint; and a support segment extending between the joint of the stylet and a proximal tip of the stylet, the support segment configured to cause the articulating segment to move between a first position and a second position, wherein the support segment includes a longitudinal split that divides the support segment into a first portion and a second portion, the first portion comprising a surface that forms a groove, and the second portion comprising a tongue configured to insert into the groove formed by the first portion.

11. The stylet of claim 10, further including:

a plurality of depth assessment bands located on the articulating segment, each depth assessment band visually distinct from an adjacent depth assessment band, a first depth assessment band located near the distal tip and having a first visual representation configured to whether an insertion depth of the distal tip is appropriate when positioned adjacent to an anatomical structure of a patient.

12. The stylet of claim 10, wherein:

the first portion comprises a first ledge;

the second portion comprises a second ledge; and the first ledge and the second ledge configured to secure the tongue of the second portion in the groove formed by the first portion.

13. The stylet of claim 10, wherein:

the first position of the articulating segment comprises a first curve; and the second position of the articulating segment comprises a second curve.

* * * * *